(12) United States Patent
Coric et al.

(10) Patent No.: US 12,121,609 B2
(45) Date of Patent: Oct. 22, 2024

(54) SUBLINGUAL FORMULATION OF RILUZOLE

(71) Applicant: Biohaven Therapeutics Ltd., New Haven, CT (US)

(72) Inventors: Vladimir Coric, Madison, CT (US); Robert Berman, Stonington, CT (US); Ronald S. Vladyka, Somerset, NJ (US); Amgad Saleh, Dayton, NJ (US); Danny Yu, Somerville, MA (US)

(73) Assignee: Biohaven Therapeutics Ltd., Tortola (VG)

( * ) Notice: Subject to any disclaimer, the term of this patent is extended or adjusted under 35 U.S.C. 154(b) by 183 days.

(21) Appl. No.: 17/079,498

(22) Filed: Oct. 25, 2020

(65) Prior Publication Data

US 2021/0038499 A1 Feb. 11, 2021

Related U.S. Application Data

(63) Continuation of application No. 15/100,160, filed as application No. PCT/US2015/061114 on Nov. 17, 2015, now Pat. No. 11,660,267.

(60) Provisional application No. 62/083,094, filed on Nov. 21, 2014.

(51) Int. Cl.

| | |
|---|---|
| *A61K 31/428* | (2006.01) |
| *A61K 9/00* | (2006.01) |
| *A61K 9/08* | (2006.01) |
| *A61K 9/20* | (2006.01) |
| *A61K 47/20* | (2006.01) |
| *A61K 47/26* | (2006.01) |
| *A61P 25/00* | (2006.01) |
| *A61P 25/16* | (2006.01) |
| *A61P 25/18* | (2006.01) |
| *A61P 25/22* | (2006.01) |
| *A61P 25/24* | (2006.01) |
| *A61P 25/28* | (2006.01) |
| *A61P 25/30* | (2006.01) |

(52) U.S. Cl.
CPC .......... *A61K 9/006* (2013.01); *A61K 9/0056* (2013.01); *A61K 9/08* (2013.01); *A61K 9/20* (2013.01); *A61K 31/428* (2013.01); *A61K 47/20* (2013.01); *A61K 47/26* (2013.01); *A61P 25/00* (2018.01); *A61P 25/16* (2018.01); *A61P 25/18* (2018.01); *A61P 25/22* (2018.01); *A61P 25/24* (2018.01); *A61P 25/28* (2018.01); *A61P 25/30* (2018.01)

(58) Field of Classification Search
CPC ...... A61K 31/428; A61K 47/20; A61K 47/26; A61K 9/0056; A61K 9/006; A61K 9/08; A61K 9/20; A61P 25/00; A61P 25/16; A61P 25/18; A61P 25/22; A61P 25/24; A61P 25/28; A61P 25/30
See application file for complete search history.

(56) References Cited

U.S. PATENT DOCUMENTS

| | | | |
|---|---|---|---|
| 4,370,338 A | 1/1983 | Mizoule | |
| 5,837,287 A | 11/1998 | Yarwood | |
| 6,432,992 B1 | 8/2002 | Aubourg | |
| 8,765,150 B2 | 7/2014 | Artico | |
| 2002/0004516 A1 | 1/2002 | Stutzmann et al. | |
| 2002/0025366 A1 | 2/2002 | Jager et al. | |
| 2014/0371277 A1 | 12/2014 | Cohen et al. | |
| 2018/0153862 A1 | 6/2018 | Coric et al. | |

FOREIGN PATENT DOCUMENTS

| | | |
|---|---|---|
| CA | 2864008 C | 9/2013 |
| EP | 2228054 A1 | 9/2010 |
| WO | 2008/127679 A1 | 10/2008 |
| WO | 2010/102923 A2 | 9/2010 |
| WO | 2013/127917 A1 | 9/2013 |

OTHER PUBLICATIONS

Lakhan (NMDA receptor activity in neuropsychiatric disorders, frontiers in Psychiatry, Jun. 2013, vol. 4, Articl 52, pp. 1-7).*
Kretschmer (Riluzole, a glutamate release inhibitor, and motor behavior, Naunyn-Schmiedeberg's Arch Pharmacol (1998) 358:181-190).*
Narang (International Journal of Pharmacy and Pharmaceutical Sciences, vol. 3, Suppl 2, 2011).*
Mahmoud, Azza A. et al. "Fast relief from migraine attacks using fast-disintegrating sublingual zolmitriptan tablets" Drug Development and Industrial Pharmacy 2012, 38(6), 762-769.
Pittenger, Christopher et al. "Riluzole in the treatment of mood and anxiety disorders" CNS Drugs 2012, 22(9), 761-786.
International Search Report dated Mar. 4, 2016 issued for the corresponding application PCT/US2015/061114 (4 pages).
Written Opinion dated Mar. 4, 2016 issued for the corresponding application PCT/US2015/061114 (6 pages).
Rodrigo Machado-Vieira et al. "The Role of the Tripartite Glutamatergic Synapse in the Pathophysiology and Therapeutics of Mood Disorders" The Neuroscientist, 2009, vol. 15, No. 5, pp. 525-539.
Marcos Emilio dos Santos Frizzo et al. "Riluzole Enhances Glutamate Uptake in Rat Astrocyte Cultures" Cellular and Molecular Neurobiology, 2004, vol. 24, No. 1, pp. 123-128.
John Wokke "Riluzole" Lancet, 1996, vol. 348, pp. 795-799.

\* cited by examiner

*Primary Examiner* — Rei Tsang Shiao

(57) ABSTRACT

Disclosed is sublingual administration of riluzole. In particular, a method for treating a neuropsychiatric disorder or symptom by administering a sublingual formulation of riluzole is provided. In addition, a method of relieving or reducing oral pain using the sublingual formulation of riluzole is disclosed.

14 Claims, No Drawings

SUBLINGUAL FORMULATION OF RILUZOLE

CROSS-REFERENCE TO RELATED APPLICATIONS

This application is a continuation of U.S. patent application Ser. No. 15/100,160 filed May 27, 2016, which is a National Stage Application under 35 U.S.C. § 371 of International Application No. PCT/US2015/061114 filed Nov. 17, 2015, which claims priority to U.S. Provisional Application No. 62/083,094, filed Nov. 21, 2014, the entire disclosure of each of which applications is incorporated herein by reference.

TECHNICAL FIELD

The present invention relates to sublingual administration of riluzole and methods using a sublingual formulation of riluzole.

BACKGROUND

Riluzole (6-(trifluoromethoxy)benzothiazol-2-amine) is a pharmaceutical which has been used for treatment of amyotrophic lateral sclerosis (ALS). Recently, riluzole has been shown to have other clinical benefits. For example, orally administered riluzole dosed twice a day at a total dose of 100 mg may relieve or treat neuropsychiatric symptoms and disorders, such as mood, anxiety disorder, refractory depression, obsessive-compulsive anxiety and the like.

However, such therapeutic neuropsychiatric effects via current oral dosing are not evident until multiple days after administration, or up to weeks, and at doses of 100 mg/day. The current oral administration is currently limited by poor solubility, variable absorption, undesirable tolerability including increased liver function abnormalities and extensive first past metabolism requiring high doses. Despite being approved for ALS, extensively researched in neuropsychiatric disorders and commercially available for over 20 years, the clinically undesirable effects of riluzole have not been overcome and have limited its use. The intrinsic property of the drug itself teaches away from the sublingual administration of riluzole. Riluzole has a very low solubility in water, poor oral palatability, pH dependent chemical stability, and intense as well as persistent numbness or burning sensation throughout the oral cavity. Techniques aimed at reducing these undesirable effects, such as use of chelating agents, would only facilitate the oral swallowing and gastric absorption rather than resulting in sublingual absorption. Novel administration of riluzole and effects thereof have not been addressed for improving therapeutic use, particularly in neuropsychiatric treatment, or to attenuate undesirable adverse effects. Further teaching away from the use of sublingual riluzole, sublingual routes of administration have been limited to delivering doses from the microgram range up to 10 mg.

As such, an alternative route for administrating riluzole for extended therapeutic and clinical use is desired.

SUMMARY OF THE INVENTION

The present invention provides: 1) a novel method of sublingual administration of riluzole to a subject, particularly to a human, in need thereof, 2) unexpected low doses of riluzole that possess therapeutic effects across disease indications including desirable neuropsychiatric effects, and 3) the ability to provide a larger than expect dose of riluzole in a sublingual formulation.

The sublingual formulation as provided in the present invention comprises an effective amount of riluzole or a pharmaceutically acceptable salts, solvate, anomers, enantiomers, hydrate or prodrugs thereof. The formulation provides sufficient solubility for riluzole to be incorporated into the sublingual formulation at relatively large doses and sublingually delivered. The formulation is preferably a modified oral disintegrating formulation of riluzole. The excipients, including mannitol and gelatin, are blended, solubilized with water and deaerated before being mixed with the active pharmaceutical ingredient (or "API"), riluzole, which has been milled separately. Particle size of the API ($D_{50}$) is less than about 2 microns. The mixture is lyophilized by flash freezing and then freeze-dried. The formulation has good oral palatability.

In another aspect, a method of treating a disease of a subject by administering the sublingual formulation is provided. The method comprises providing a sublingual formulation made using the process described herein having an effective amount of riluzole or a pharmaceutically acceptable salts, solvate, anomers, enantiomers, hydrate or prodrugs thereof, and administering the formulation to a subject to treat the disease state. The riluzole is preferably delivered in a once per day format but if needed, two or more doses per day may be used.

The subject may be a human.

The disease may be a neuropsychiatric disorder or symptom. In particular, the neuropsychiatric disorder may be anxiety disorders, generalized anxiety disorder, panic disorder, social anxiety, mood disorders, cognitive disorders, schizophrenia, dementia, agitation, apathy, anxiety, psychoses, post-traumatic stress disorders, irritability, disinhibition, learning disorders, memory loss, personality disorders, bipolar disorders, obsessive-compulsive disorders, autism, Rett syndrome, eating disorders, conduct disorders in DSM-5 and or combinations thereof. The disease state may also include neurodegenerative disorders, pain disorders, ALS, cerebellar ataxia, other ataxia, Huntington's disease, Parkinson's disease, supranuclear palsy, frontotemporal dementia, frontotemporal lobar degeneration, delirium, Alzheimer's disease, mild cognitive impairment, mild cognitive impairment due to Alzheimer's disease, drug addiction, tinnitus, and mental retardation.

In addition, the neuropsychiatric symptom may be anxiety, depression, stress, fatigue, feelings of panic, fear, uneasiness, problems in sleeping, cold or sweaty hands and/or feet, mood liability, mania, impaired concentration or attention, cognitive problems, obsessions, compulsions, repetitive behaviors, aggression, social phobias or impairments, stage fright, shortness of breath, heart palpitations, an inability to be still and calm, dry mouth, numbness or tingling in the hands or feet, nausea, muscle tension, dizziness apathy, elation, disinhibition, irritability, wandering, irritable bowel, belly pain, belly discomfort, diarrhea, change in bowel habits, abdominal bloating, abdominal gas, abdominal bloating, constipation or combinations thereof.

The effective amount of riluzole for the sublingual formulation of the present invention to achieve a lower therapeutic dose may be less than that of orally administered riluzole. Moreover, effective dose of the sublingual formulation of the riluzole may be about 1 to 95% of that of the orally administered riluzole.

The sublingual formulation of riluzole may produce a rapid therapeutic onset of action within minutes or an onset that is quicker than the orally swallowed dose. Further, the sublingual formulation of riluzole is associated with minimal or no oral numbness. The palatability is also good while still resulting in sublingual absorption.

According to the present invention, the method of treating the disease of the subject by administering the sublingual formulation may reduce side effects of riluzole including attenuates liver function abnormalities, which is associated with the orally administered riluzole. According to the present invention, the method of treating the disease of the subject by administering the sublingual formulation may reduce the total drug load necessary to result in a therapeutic effect. A lower sublingual dose of the formulation may deliver similar effects compared to a higher oral dose or even enhanced effects compared to a higher oral dose.

The sublingual formulation for treating neuropsychiatric disorders or symptoms may be dosed at or below about 200 mg/day, at or below about 150 mg/day, at or below about 100 mg/day, at or below about 70 mg/day, at or below about 60 mg/day, at or below about 50 mg/day, at or below about 42.5 mg/day, at or below about 37.5 mg/day at or below about 35 mg/day, at or below about 20 mg/day, at or below about 17.5 mg/day, at or below about 15 mg/day, at or below about 10 mg/day, at or below about 5 mg/day, or at or below about 1 mg/day.

According to the method of the present invention, a therapeutic effect may begin within about 30 min after administration, within about 20 min after administration, within about 15 min after administration, within about 10 min after administration, within within about 5 min after administration, within about 4 min after administration, within about 3 min after administration, within about 2 min after administration, or within about 1 min after administration.

The method of treating a disease of a subject by administering a sublingual formulation may further comprise using the sublingual formulation including a riluzole prodrug, which may help to minimize parethesias or numbness associated with the riluzole.

In still another aspect, a method of relieving or reducing oral pain of a subject is provided. The method may comprise administering an effective amount of riluzole or a pharmaceutically acceptable salts, solvate, anomers, hydrate or prodrugs thereof in the oral cavity. Alternatively, a method of relieving or reducing oral pain of a subject by administering a sublingual formulation comprising an effective amount of riluzole or a pharmaceutically acceptable salts, solvate, anomers, hydrate or prodrugs thereof.

Although the sublingual formulation may cause numbness or parethesias, the effect is normally nominal and well tolerated.

A treatment area of oral pain may be throughout an oral cavity including the upper surface of the tongue, lips, buccal area, back of throat, entire oral cavity or combinations thereof. In addition, the oral pain for treatment is caused by infection, inflammation, burn, cut, toothache, sore gums, canker sores, braces, minor dental procedures, denture irritation, oral surgery, neurologic disorders, disorders of the mucosa, oral ulcers, chemotherapy agents or combinations thereof.

A therapeutic effect begins within about 30 min after administration, within 20 min after administration, within about 15 minute after administration, within about 10 min after administration, within about 5 min after administration, within about 4 min after administration, within about 3 min after administration, within about 2 min after administration, or within about 1 min after administration.

The sublingual formulation for treating oral pain may be dosed at or below about 200 mg/day, at or below about 100 mg/day, at or below about 70 mg/day, at or below about 50 mg/day, at or below about 42.5 mg/day, at or below about 37.5 mg mg/day, at or below about 35 mg/day, at or below about 20 mg/day, at or below about 15 mg/day, at or below about 10 mg/day, or at or below about 5 mg/day.

According to various exemplary embodiments, the sublingual formulation may have a greater $C_{max}$ or greater dose normalized $C_{max}$ than the orally administered riluzole to provide a therapeutically beneficial effect. Moreover, the sublingual formulation of the present invention may have a lesser or earlier $T_{max}$ than orally administered riluzole to provide a therapeutically beneficial effect. In addition, the sublingual formulation may have a greater AUC per milligram of the riluzole than the orally administered riluzole. The greater AUC per milligram may be measured in partial $AUC_{0-0.5\ h}$, $AUC_{0-1\ h}$, $AUC_{0-2\ h}$, $AUC_{0-12\ h}$, $AUC_{0-t}$ or $AUC_{0-inf}$.

The present invention also provides a sublingual or sustained release formulation which may comprise an effective amount of riluzole or a pharmaceutically acceptable salts, solvate, anomers, enantiomers, hydrate or prodrugs thereof to treat irritable bowel syndrome. The present invention also provides a sublingual or sustained release formulation which may comprise an effective amount of riluzole or a pharmaceutically acceptable salts, solvate, anomers, enantiomers, hydrate or prodrugs thereof to treat cancers such as gliomas, glioblastoma or melanoma. The present invention also provides a sublingual or sustained release formulation which may comprise an effective amount of riluzole or a pharmaceutically acceptable salts, solvate, anomers, enantiomers, hydrate or prodrugs thereof to treat cancers in combination with immunotherapies (including alone or in combination with vaccines, anti-PD1, anti-PDL1, anti-CTLA4 or other immunotherapy or checkpoint inhibitor targets including: CTLA4, cytotoxic T-lymphocyte-associated antigen 4; Ig, immunoglobulin; LAG3, lymphocyte activation gene 3; mAbs, monoclonal antibodies; PD1, programmed cell death protein 1; PDL, PD1 ligand; TIM3, T cell membrane protein 3, CD40L, A2aR, adenosine A2a receptor; B7RP1, B7-related protein 1; BTLA, B and T lymphocyte attenuator; GAL9, galectin 9; HVEM, herpesvirus entry mediator; ICOS, inducible T cell co-stimulator; IL, interleukin; KIR, killer cell immunoglobulin-like receptor; LAG3, lymphocyte activation gene 3; PD1, programmed cell death protein 1; PDL, PD1 ligand; TGFβ, transforming growth factor-0; TIM3, T cell membrane protein 3; CD27).

Other aspects of the invention are disclosed herein.

DETAILED DESCRIPTION OF THE INVENTION

The following is a detailed description provided to aid those skilled in the art in practicing the present invention. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description is for describing particular embodiments only and is not intended to be limiting. All publications, patent applications, patents, FIGURES and other references mentioned herein are expressly incorporated by reference in their entirety.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The term "riluzole", as used herein, refers to a drug having a chemical structure as follows. It is currently available in the market as RILUTEK®. The term "riluzole" also refers to all prodrugs, enantiomers, or derivatives and its pharmaceutically acceptable salts.

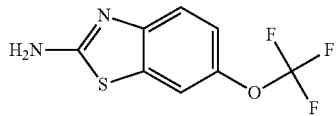 [SMILES: Nc1nc2ccc(OC(F)(F)F)cc2s1]

6-(trifluoromethoxy)benzothiazol-2-amine

The term "sublingual administration", as used herein, refers to a route of administrating a chemical agent or a drug by placing thereof under a tongue of a subject.

The term "prodrug" as used herein, is a precursor of a drug which may be administered in an altered or less active form. The prodrug may be converted into the active drug form in physiological environments by hydrolysis or other metabolic pathways.

The term "riluzole prodrug" refers to a compound which is a derivative from riluzole with modification therein. A riluzole prodrug may also refer to a compound that is metabolized into an active form of riluzole by the body.

The term "ALS", as used herein, means Amyotrophic Lateral Sclerosis.

The term "neuropsychiatric disorder", as used herein, is a mental or neurologic disorder which is associated with the nervous system. For example, the neuropsychiatric disorder may include anxiety disorders, mood disorders, neurodegenerative disorders, neurodevelopmental disorders, autism, pervasive developmental disorder, pain disorders, neuropathic pain, ALS, cognitive disorders, Huntington's disease, Parkinson's disease, supranuclear palsy, frontotemporal dementia, frontotemporal lobar degeneration, delirium, Alzheimer's disease, mild cognitive impairment, mild cognitive impairment due to Alzheimer's disease, depression, mania, attention deficit disorders, drug addiction, dementia, agitation, apathy, anxiety, psychoses, post-traumatic stress disorders, irritability, and disinhibition, learning disorders, memory loss, mental retardation, dementia, personality disorders, bipolar disorders, bipolar depression, generalized anxiety disorder, panic disorder, obsessive-compulsive disorders, trichotillomania, eating disorders, and the like. More specifically, neuropsychiatric disorders includes those listed in the Diagnostic and Statistical Manual of Mental Disorders (American Psychiatric Association, 5$^{th}$ Edition): Neurodevelopmental disorders, Intellectual disabilities, Intellectual disability (intellectual developmental disorder), Global developmental delay, Unspecified intellectual disability (Intellectual developmental disorder), Communication disorders, Language disorder, Speech sound disorder, Childhood-onset fluency disorder (stuttering), Social (pragmatic) communication disorder, Unspecified communication disorder, Autism spectrum disorder, Rett Syndrome, Attention deficit hyperactivity disorder (ADHD), Unspecified attention-deficit/Hyperactivity disorder, Specific learning disorder, Motor disorders, Developmental coordination disorder, Stereotypic movement disorder, Tic disorders, Tourette's disorder, Persistent (Chronic) motor or vocal tic disorder, Provisional tic disorder, Other specified tic disorder, Unspecified tic disorder, Other neurodevelopmental disorders, Unspecified neurodevelopmental disorder, Schizophrenia spectrum and other psychotic disorders, Delusional disorder, Brief psychotic disorder, Schizophreniform disorder, Schizophrenia, Schizoaffective disorder, Major depressive or manic mood disorder concurrent with primary symptoms of schizophrenia, Substance/Medication-induced psychotic disorder, Psychotic disorder due to another medical condition, Catatonia, Other specified schizophrenia spectrum and other psychotic disorder, Unspecified schizophrenia spectrum and other psychotic disorder, Bipolar and related disorders, Anxiety disorders, Obsessive-compulsive and related disorders, Trauma- and stressor-related disorders, Reactive attachment disorder, Disinhibited social engagement disorder, Posttraumatic stress disorder, Acute stress disorder, Adjustment disorder, Other specified Trauma- and stressor-related disorder, Unspecified trauma- and stressor-related disorder, Dissociative disorders, Dissociative identity disorder, Dissociative amnesia, Depersonalization/Derealization disorder, Somatic symptom disorders, Encopresis, other elimination disorder, Disruptive, impulse-control and conduct disorders in DSM-5, Oppositional defiant disorder, Intermittent explosive disorder, Conduct disorder, Other specified disruptive, conduct disorder, unspecified disruptive, and conduct disorder, Substance-Related and Addictive Disorders, Substance-Related Disorders, Alcohol-Related Disorders, Alcohol Use Disorder, Alcohol Withdrawal, Cannabis-Related Disorders, Cannabis Use Disorder, Gambling Disorder, Cluster A personality disorders, Paranoid personality disorder, Schizoid personality disorder, Schizotypal personality disorder, Cluster B personality disorders, Antisocial personality disorder, Borderline personality disorder, Histrionic personality disorder, Narcissistic personality disorder, Cluster C personality disorders, Avoidant personality disorder, Dependent personality disorder, Obsessive-compulsive personality disorder, Paraphilic disorders.

The term "DSM" refers to a Diagnostic and Statistical Manual of Mental Disorders as provided by American Psychiatric Association's (APA) classification and diagnostic tool. Diagnostic and Statistical Manual of Mental Disorders, Fifth Edition (DSM-5 or DSM-V) is updated in 2013 and exemplary disorders in DSM-V are listed in Appendix A. In addition, the DSM-V has a structure that includes broad categories and subdiagnoses indicating disorders, conditions and problems.

"Neuropsychiatric disorders" could also include neurodegenerative or neurologic disorders including: Alzheimer's disease, dementia, vascular dementia, mixed dementia, Parkinson's disease, Huntington's disease, Amyotrophic lateral sclerosis (ALS), pseudobulbar affect, agitation in Alzheimer's disease, cerebellar ataxia, hereditary ataxias, multiple sclerosis, Progressive Supranuclear Palsy, pain disorders, neuropathic pain, neuropathies, stroke, seizure, Fragile X, tinnitus, and similar conditions.

The neuropsychiatric symptoms may include anxiety, depression, stress, fatigue, feelings of panic, fear, uneasiness, problems in sleeping, cold or sweaty hands and/or feet, shortness of breath, heart palpitations, social phobia, fear of public speaking, an inability to be still and calm, dry mouth, numbness or tingling in the hands or feet, nausea, muscle tension, dizziness apathy, elation, disinhibition, irritability, wandering, and the like. Additionally, neuropsychiatric symptoms could include: delusions, hallucinations, disorganized thinking or speech, derailment of focal topic or loose associations, incoherence, grossly disorganized or abnormal motor behavior (including catatonia), negative symptoms—reduced emotional expression, avolition, alogia, anhedonia, associality, dyskinesias (including tardive dyskinesia), anhedonia and dysphoria, anger and aggression, or symptoms of dissociation, or some combination of these.

Other disorders treated could include cancer (including Acute Lymphoblastic Leukemia (ALL), Acute Myeloid Leukemia (AML), Adrenocortical Carcinoms, Childhood cancers, AIDS-Related Cancers, Kaposi Sarcoma, AIDS-Related Lymphoma, Primary CNS Lymphoma, Anal Cancer, Astrocytomas, Atypical Teratoid/Rhabdoid Tumor, Basal Cell Carcinoma, Skin Cancer (Nonmelanoma), Bile Duct Cancer, Bladder Cancer, Bone Cancer, Ewing Sarcoma Family of Tumors, Osteosarcoma and Malignant Fibrous Histiocytoma, Brain Stem Glioma, Atypical Teratoid/Rhabdoid Tumor, Embryonal Tumors, Germ Cell Tumors, Craniopharyngioma, Ependymoma, Breast Cancer, Bronchial Tumors, Burkitt Lymphoma, Non-Hodgkin Lymphoma, Carcinoid Tumor, Gastrointestinal Carcinoma, Cardiac (Heart) Tumors, Primary Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Mycosis Fungoides and Sezary Syndrome, Ductal Carcinoma In Situ (DCIS), Embryonal Tumors, Endometrial Cancer, Ependymoma, Esophageal Cancer, Esthesioneuroblastoma, Extracranial Germ Cell Tumor, Extragonadal Germ Cell Tumor, Eye Cancer, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST), Germ Cell Tumor, Ovarian, Testicular, Gestational Trophoblastic Disease, Glioma, Hairy Cell Leukemia, Head and Neck Cancer, Hepatocellular (Liver) Cancer, Histiocytosis, Langerhans Cell, Hodgkin Lymphoma, Hypopharyngeal Cancer, Islet Cell Tumors, Pancreatic Neuroendocrine Tumors, Kaposi Sarcoma, Kidney, Renal Cell, Wilms Tumor, Langerhans Cell Histiocytosis, Laryngeal Cancer, Leukemia, Acute Lymphoblastic (ALL), Acute Myeloid (AML), Chronic Lymphocytic (CLL), Chronic Myelogenous (CML), Hairy Cell, Lip and Oral Cavity Cancer, Liver Cancer (Primary), Lung Cancer, Non-Small Cell, Small Cell, Lymphoma, Hodgkin, Non-Hodgkin, Macroglobulinemia, Waldenström, Male Breast Cancer, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML) Myeloma, Multiple, Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Ovarian Cancer, Low Malignant Potential Tumor, Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Rhabdomyosarcoma, Uterine, Small Intestine Cancer, Soft Tissue Sarcoma, Sqamous Cell Carcinoma, Squamous Neck Cancer with Occult Primary, Metastatic, Ttomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Unknown Primary, Ureter and Renal Pelvis, Transitional Cell Cancer, Urethral Cancer, Uterine Cancer, Endometrial, Uterine Sarcoma, Vaginal Cancer, Vulvar Cancer, Waldenström Macroglobulinemia, Wilms Tumor.

The term "treatment" as used herein includes any treatment of a condition or disease in a subject, or particularly a human, and may include: (i) preventing the disease or condition from occurring in the subject which may be predisposed to the disease but has not yet been diagnosed as having it; (ii) inhibiting the disease or condition, i.e., arresting its development; relieving the disease or condition, i.e., causing regression of the condition; or (iii) ameliorating or relieving the conditions caused by the disease, i.e., symptoms of the disease. "Treatment," as used herein, could be used in combination with other standard therapies or alone.

The term "effective" is used to describe an amount of a compound, composition or component which, when used within the context of its intended use, effects an intended result.

The term "effective amount" refers to that amount which is sufficient to effect treatment, as defined herein, when administered to a subject in need of such treatment. The effective amount will vary depending on the subject and disease state being treated, the severity of the affliction and the manner of administration, and may be determined routinely by one of ordinary skill in the art.

The term "pharmaceutically acceptable salt" is used throughout the specification to describe, where applicable, a salt form of one or more of the compounds or prodrugs described herein which are presented to increase the solubility of the compound in the gastric or gastroenteric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present invention. In a preferred embodiment, the description provides pharmaceutically acceptable salts of the modified peptides as described herein, which retain the biological effectiveness and properties of the parent compounds and which are not biologically or otherwise harmful as the dosage administered. The compounds of this invention are capable of forming both acid and base salts by virtue of the presence of amino and carboxy groups respectively.

The term "$C_{max}$", as used herein, refers to a maximum concentration of a drug in blood, serum, a specified compartment or test area of a subject between administration of a first dose and administration of a second dose. The term $C_{max}$ could also refer to dose normalized ratios if specified.

The term "$T_{max}$", as used herein, refers to a time or period after administration of a drug when the maximum concentration ($C_{max}$) is reached in blood, serum, a specified compartment or test area of a subject.

The term "AUC" (area under the curve), as used herein, refers to a total amount of drug absorbed or exposed to a subject. Generally, AUC may be obtained from mathematical method in a plot of drug concentration in the subject over time until the concentration is negligible. The term "AUC" (area under the curve) could also refer to partial AUC at specified time intervals (as may be the case with sublingual absorption which would increase AUC at earlier time intervals).

Sublingual Formulation of Riluzole

The invention relates to a sublingual formulation of riluzole. The sublingual formulation may be administered in an effective amount to a subject in need thereof. The subject may be an animal or human.

According to the current invention, the riluzole or its pharmaceutically acceptable salts thereof may be formulated in a pharmaceutical composition suitable for sublingual administration.

Riluzole and the pharmaceutically acceptable salts thereof can be formulated using pharmaceutically acceptable carriers well known in the art into dosages suitable for sublingual or buccal administration. Such carriers enable the riluzole for sublingual administration to be formulated in dosage forms such as tablets, powders, pills, capsules, liquids, gels, syrups, slurries, suspensions, and the like, for sublingual absorption by a subject to be treated. These carriers may be, but not limited to, selected from sugars, starches, cellulose and its derivatives, malt, gelatin, talc, calcium sulphate, vegetable oils, synthetic oils, polyols, alginic acid, phosphate buffered solutions, emulsifiers, isotonic saline, pyrogen-free water and combinations thereof. In particular, any form of substance may be accepted to sublingual administration if it dissolves easily in saliva.

The sublingually administered chemical agent or the drug can diffuse into capillaries through mucous membrane under the tongue, and then enter venous circulation of the subject. As such, sublingual administration may have advantages over oral administration as allowing for direct or faster entry to venous circulation, without risks of degradation in gastrointestinal tract, alteration by drug metabolism in liver and the like. Various drugs in the market are designed for sublingual administration. Riluzole is generally used to treat amyotrophic lateral sclerosis (ALS). However, other uses have been found, and in particular, riluzole or prodrugs of riluzole or pharmaceutically acceptable salts thereof is subjected to a sublingual administration for the treatment of neuropsychiatric disorders. The sublingual administration may also be used for other neuropsychiatric disorders or relieving or reducing pain. In some instances, the preferred effect is on oral pain.

The pharmaceutical composition may include an approved pharmaceutical ingredient, i.e., riluzole, in an effective amount to achieve their intended purpose. For example, the dose of the riluzole administered sublingually to the subject should be sufficient to provide a beneficial response in the subject over time such as reduction in symptoms.

The quantity of the riluzole to be administered may depend on the subject to be treated inclusive of the age, sex, weight and general health condition thereof. In this regard, precise amounts of the agent(s) for administration will depend on the judgement of the practitioner. In determining the effective amount of the riluzole to be administered in the treatment or reducing of the conditions associated with the neuropsychiatric symptoms and disorders, the physician may evaluate clinical factors including symptoms severity or progression of the disorder. In some conditions, a rapid absorption of riluzole may be desirable. In any event, those of skill in the art may readily determine suitable dosages of the chemical agents of the invention.

The pharmaceutical composition also includes other pharmaceutically acceptable carriers and/or excipients such as binders, lubricants, diluents, coatings, disintegrants, barrier layer components, glidants, colouring agents, solubility enhancers, gelling agents, fillers, proteins, co-factors, emulsifiers, solubilising agents, suspending agents and mixtures thereof. A skilled artisan in the art would know what other pharmaceutically acceptable carriers and/or excipients could be included in the formulations according to the invention. The choice of excipients would depend on the characteristics of the compositions and on the nature of other pharmacologically active compounds in the formulation. Appropriate excipients are known to those skilled in the art (see Handbook Of Pharmaceutical Excipients, fifth edition, 2005 edited by Rowe et al., McGraw Hill) and have been utilized to yield a novel sublingual formulation with unexpected properties.

In addition, the pharmaceutical composition for sublingual use can be obtained by combining the approved pharmaceutical ingredient, i.e., riluzole, with further excipients, with optionally processing to obtain dosage forms such as tablets, powders, pills, capsules, liquids, gels, syrups, slurries, suspensions, and the like, for sublingual absorption by a subject to be treated. Suitable excipients may be, but not limited to, fillers such as sugars, including lactose, sucrose, mannitol, or sorbitol; cellulose preparations such as maize starch, wheat starch, rice starch, potato starch, gelatin, gum tragacanth, methyl cellulose, hydroxypropyl methyl-cellulose, sodium carboxymethylcellulose, and/or polyvinyl-pyrrolidone (PVP). If desired, disintegrating agents may be combined as well, and exemplary disintegrating agents may be, but not limited to, cross-linked polyvinyl pyrrolidone, agar, or alginic acid or a salt thereof such as sodium alginate. The compositions may be prepared by any of the methods of pharmacy but all methods include the step of bringing into association one or more chemical agents as described above with the carrier which constitutes one or more necessary ingredients. In general, the pharmaceutical compositions of the present invention may be manufactured in conventional methods known in the art, for example, by means of conventional mixing, dissolving, granulating, dragee-making, levigating, emulsifying, encapsulating, entrapping, lyophilising processes and the like.

The sublingual formulation of the invention may be prepared in a form of an orally dissolving or disintegrating tablet (ODT). The ODT as used herein may be prepared by mixing the riluzole with water-soluble diluents and compressed in a tablet. A suspension comprising riluzole may be prepared with appropriate excipients and the riluzole suspension may be dispensed into blister packs and freeze-dried. An exemplary freeze-dried preparation platform that could be used for the riluzole ODT is the ZYDIS® (Catalent, Somerset, NJ, USA) formulation. In particular, the excipients, including water, are blended and the riluzole is separately milled to size and mixed with the excipients. The suspension then undergoes lyophilisation by flash freezing and freeze drying. Other methods of preparing ODTs may be used without limitation, and detailed description of general methods thereof have been disclosed, for example, in U.S. Pat. Nos. 5,631,023; 5,837,287; 6,149,938; 6,212,791; 6,284,270; 6,316,029; 6,465,010; 6,471,992; 6,471,992; 6,509,040; 6,814,978; 6,908,626; 6,908,626; 6,982,251; 7,282,217; 7,425,341; 7,939,105; 7,993,674; 8,048,449; 8,127,516; 8,158,152; 8,221,480; 8,256,233; and 8,313,768, each of which is incorporated herein by reference in its entirety.

The sublingual formulation of the invention may comprise riluzole or an effective amount of a riluzole prodrug. The riluzole prodrug may be similar or less active form of riluzole. The riluzole prodrug may have improved physiochemical, physiological pharmacokinetic or therapeutical characteristics when administered sublingually. The riluzole prodrug may reduce side effects when orally or sublingually administered. In particular, the numbness or parethesias that can occur when riluzole is administered orally or sublingually may be reduced or eliminated by using the riluzole prodrug instead of riluzole.

The clinical or therapeutic effect of the riluzole sublingually formulated may have an improved pharmacokinetic profile for the pharmaceutical agent as measured by standard testing parameters. When the riluzole is administered sublingually, the $T_{max}$, $C_{max}$ and AUC of the drug may be improved compared to the same dose of the orally administered riluzole. For example, the sublingual formulation of the riluzole may have a greater $C_{max}$ than the orally administered riluzole to provide a therapeutically beneficial effect. The sublingual formulation of the riluzole may have an earlier or lesser $T_{max}$ than the orally administered riluzole to provide a therapeutically beneficial effect and in some instances, a more rapid therapeutic effect. Alternatively, the sublingual formulation of the riluzole may have a greater AUC per milligram of the riluzole than the orally administered riluzole.

Method of Treating a Disease

The invention also provides a method of treating a disease. The method comprises administering sublingually an effective amount of riluzole or pharmaceutically acceptable salts thereof to a subject in need thereof.

Identifying the subject in need of such treatment can be in the judgment of the subject or a health care professional and can be subjective (e.g., opinion) or objective (e.g., measurable by a test or diagnostic method). The identified subject may be an animal or human in need thereof, particularly a human. Such treatment will be suitably administered to subjects, particularly humans, suffering from the disease.

The disease from which the subject may be suffered may be a neuropsychiatric disorder or symptom. Exemplary neuropsychiatric disorder may be anxiety disorders, mood disorders, neurodegenerative disorders, pain disorders, ALS, cognitive disorders, Huntington's disease, Parkinson's disease, supranuclear palsy, frontotemporal dementia, frontotemporal lobar degeneration, delirium, Alzheimer's disease, mild cognitive impairment, mild cognitive impairment due to Alzheimer's disease, depression, mania, attention deficit disorders, drug addiction, dementia, agitation, apathy, anxiety, psychoses, post-traumatic stress disorders, irritability, and disinhibition, learning disorders, memory loss, mental retardation, dementia, personality disorders, bipolar disorders, obsessive-compulsive disorders, eating disorders, and the like. Exemplary neuropsychiatric symptoms may be anxiety, depression, stress, fatigue, feelings of panic, fear, uneasiness, problems in sleeping, cold or sweaty hands and/or feet, shortness of breath, heart palpitations, an inability to be still and calm, dry mouth, numbness or tingling in the hands or feet, nausea, muscle tension, dizziness apathy, elation, disinhibition, irritability, wandering, or combinations thereof.

The effective amount of the riluzole may be determined by the degree of a therapeutic effect, such as anxiolytic, antidepressant, mood stabilizing, stress resilient or stress relieving, anti-pain, or combinations thereof. Further, the effect of sublingual administration of riluzole may be also be indicated by unexpected and novel properties including, but not limited to: a) an attenuated or improved side effect or tolerability profile compared to oral dosing; b) rapid onset of therapeutic action; c) decreased liver function abnormalities; d) a unique pharmacokinetic profile compared to oral administration; e) a lower therapeutic dose compared that typical oral dosing; f) once daily dosing; and g) minimized or absent oral parenthesis or numbing.

The effective amount will vary depending on the subject and disease state being treated, the severity of the affliction and the manner of administration, and may be determined routinely by one of ordinary skill in the art.

The therapeutic effect of the riluzole may be evident to occur within about a few minutes to about an hour after sublingual administration thereof. In particular, the therapeutic effect may begin within about 1 minute, within about 2 minutes, within about 3 minutes, within about 4 minutes, within about 5 minutes, within about 6 minutes, within about 7 minutes, within about 8 minutes, within about 9 minutes, within about 10 minutes, within about 11 minutes, within about 12 minutes, within about 13 minutes, within about 14 minutes, within about 15 minutes, within about 16 minutes, within about 17 minutes, within about 18 minutes, within about 20 minutes, within about 60 minutes, or within about 90 minutes after administration.

The effects of the riluzole may be maintained for about 1 hour, for about 2 hours, for about 3 hours, for about 4 hours, for about 5 hours, for about 6 hours m for about 7 hours, for about 8 hours, for about 9 hours, for about 10 hours, for about 12 hours, for about 14 hours, for about 16 hours, for about 18 hours, for about 20 hours, for about 22 hours, for about 24 hours, for about 2 days, or for about 3 days or more after sublingual administration thereof.

The effective amount or dose of riluzole for sublingual administration may be less than that of orally administered riluzole. In particular, the effective dose in sublingual administration of riluzole may be of about 1-95% of the dose of the orally administered riluzole.

The effective amount of the riluzole or pharmaceutically acceptable salts thereof in sublingual administration for treatment of neuropsychiatric disorders may be dosed at or less than about 200 mg/day, at or below about 150 mg/day, at or less than about 100 mg/day, at or less than about 90 mg/day, at or less than about 80 mg/day, at or less than about 70 mg/day, at or less than about 60 mg/day, at or less than about 50 mg/day, at or less than about 40 mg/day, at or less than about 37.5 mg/day, at or less than about 35 mg/day, at or less than about 30 mg/day, at or less than about 20 mg/day, at or less than about 17.5 mg/day, at or less than about 15 mg/day, at or less than about 10 mg/day, at or less than about 9 mg/day, at or less than about 8 mg/day, at or less than about 7 mg/day, at or less than about 6 mg/day, at or less than about 5 mg/day, at or less than about 4 mg/day, at or less than about 3 mg/day, at or less than about 2 mg/day, or at or less than about 1 mg/day.

Optional dosage frequencies include once a day, twice a day, three times a day, four times a day, once every other day, once a week, twice a week, three times a week, four times a week, once every two weeks, once or twice monthly, and the like.

The clinical or therapeutic effect of the riluzole sublingually formulated and administered for neuropsychiatric disorders or symptoms may have an improved pharmacokinetic profile for the pharmaceutical agent as measured by standard testing parameters. When the riluzole is administered sublingually, the $T_{max}$, $C_{max}$ or AUC of the drug may be improved compared to the same dose of the orally administered riluzole. For example, the sublingual administration of the riluzole may have a greater $C_{max}$ than the orally administered riluzole to provide a therapeutically beneficial effect. The sublingual administration of the riluzole has a less $T_{max}$ than the orally administered riluzole to provide a therapeutically beneficial effect. Alternatively, the sublingual administration of the riluzole may have a greater AUC per milligram of the riluzole than the orally administered riluzole.

In some embodiments, the orally disintegrating formulation would be a prodrug that could be sublingually administered or even orally dispersed then swallowed with enhanced pharmacokinetic properties.

Sublingual Formulation for Oral Pain

The current invention further includes a method of sublingually administering the riluzole to the subject to produce other desired effects.

A method is provided of relieving or reducing oral pain by sublingual administration of riluzole. The method comprises administering a sublingual formulation having an effective amount of riluzole to a subject in need thereof. In certain embodiments, the subject may be an animal or human.

In certain embodiments, the sublingual formulation may induce numbness from the deposition site thereof. The numbness may be effective to reduce or relieve oral pain and spread throughout the mucosal contacts. A level of numbness may be in a tolerable range to the subject.

A treatment area of oral pain may be, but not limited to, throughout an oral cavity including the upper surface of the tongue, lips, buccal area, back of throat, entire oral cavity and the like. The oral pain for treatment may be caused by infection, viruses, inflammation, burn, cut, toothache, sore gums, canker sores, braces, minor dental procedures, denture irritation, oral surgery, neurologic disorders, disorders of the mucosa or caused by other drugs known to induce painful oral ulcers (such as chemotherapy agents).

The effects of reducing oral pain may occur within a minute or about a few minutes to about an hour. In particular, the numbness may begin within about 1 minute, within about 2 minutes, within about 3 minutes, within about 4 minutes, within about 5 minutes, within about 6 minutes, within about 7 minutes, within about 8 minutes, within about 9 minutes, within about 10 minutes, within about 11 minutes, within about 12 minutes, within about 13 minutes, within about 14 minutes, within about 15 minutes, within about 16 minutes, within about 17 minutes, or within about 18 minutes, within about 19 minutes, or within about 20 minutes after administration.

The effects of relieving or reducing oral pain may be maintained for about 1 hour, for about 2 hours, for about 3 hours, for about 4 hours, for about 5 hours, for about 6 hours m for about 7 hours, for about 8 hours, for about 9 hours, for about 10 hours, for about 12 hours, for about 14 hours, for about 16 hours, for about 18 hours, for about 20 hours, for about 22 hours, for about 24 hours, for about 2 days, or for about 3 days after sublingual administration thereof.

The sublingual administration of riluzole for relieving or reducing oral pain may be dosed at or less than about 200 mg/day, at or less than about 150 mg/day, at or less than about 100 mg/day, at or less than about 90 mg/day, at or less than about 80 mg/day, at or less than about 70 mg/day, at or less than about 60 mg/day, at or less than about 50 mg/day, at or less than about 40 mg/day, at or less than about 35 mg/day, at or less than about 30 mg/day, at or less than about 20 mg/day, at or less than about 17.5 mg/day, at or less than about 10 mg/day, at or less than about 9 mg/day, at or less than about 8 mg/day, at or less than about 7 mg/day, at or less than about 6 mg/day, at or less than about 5 mg/day, at or less than about 4 mg/day, at or less than about 3 mg/day, at or less than about 2 mg/day, or at or less than about 1 mg/day.

Optional dosage frequencies include once a day, twice a day, three times a day, four times a day, once a week, twice a week, three times a week, four times a week, once every two weeks, once or twice monthly, and the like.

The formulation for relieving or reducing oral pain may comprise an effective amount of riluzole and a pharmaceutically acceptable carrier thereof. The pharmaceutical composition can be formulated as tablets, powders, pills, capsules, liquids, gels, ointments, syrups, slurries, suspensions, and the like, to provide substantial absorption rate at the treated area. An additional bioactive agent or other drugs may be added to a pharmaceutical composition for effective and elevated effects of pain relief. In some embodiments the formulation may be administered topically in the oral cavity or buccal mucosa.

EXAMPLES

The following examples illustrate the invention and are not intended to limit the scope of the invention.

Example 1

A 51 year-old male was administrated with riluzole on four occasions.

(1) An oral administration of riluzole was used as a comparator. A standard 50 mg riluzole tablet (a tablet not of the present invention) was pulverized and administered into the mouth cavity for 40 seconds to allow for transmucosal and/or oral absorption. This was not sublingual or buccal administration. There were no acute or chronic effects on neuropsychiatric domains. More specifically, there were no effects on mood, anxiety or behavior. Prominent oral numbness was noted. Within the first minute, a sensation of numbness spread throughout the oral cavity including the upper surface of the tongue and lips, resulting in circumoral paresthesias. The effects were moderate and peaked within 4 minutes. The effects lasted for up to 80 minutes. The effects started subsiding after 15 minutes and were considered mild after 40 minutes and minimal after 80 minutes. All effects were limited to local mouth-related sensations described above.

(2) Separately, a first sublingual administration of a formulation of the invention was performed. About 70 mg of the sublingual formulation of riluzole was placed under the tongue of the subject and held firmly in place. Unexpectedly, the subject experienced acute psychotropic effects shortly after the sublingual administration. Within approximately 40 minutes from the sublingual administration, the subject experienced a sense of enhanced or improved mood. The subject noted a sense of well-being and conveyed a sense of optimism that represented a change from the baseline mood state. The mood state change was estimated to last at least four hours.

Within one minute of sublingual administration, tongue numbness developed, and, after 4 minutes, numbness spread over the lips as well as the back of the throat. The numbness reached to a moderate level in 16 minutes, lessened to a mild level by 20 minutes, and fully dissipated over the next hour. The numbness associated with the sublingual administration was significantly attenuated compared to the diffuse oral pulverized administration described previously. The sublingual formulation yielded a mild and not bothersome numbness that was localized (versus the pulverized riluzole tablet that was more intense, bothersome and generalized).

(3) A second sublingual administration occurred on another day. About 70 mg of a sublingual formulation of riluzole was placed under the tongue of the subject for about 95 seconds until fully dissolved. Again, the subject experienced a similar improvement in mood. The subject reported a sense of optimism and well-being. These feelings peaked by 40 minutes. After 25 minutes, the subject reported feeling relaxed (less anxious) and with an increased level of alertness. The subject reported improved sleep condition and vivid dreams that evening.

Tongue and lip numbness was noted after about 4 minutes, peaked after 6 minutes with a moderate level of numbness and waned thereafter to a mild level by about 24 minutes. The mouth numbness was considered very mild to minimal at this time point. Again, the oral numbness was attenuated compared to the diffuse oral administration of the pulverized standard riluzole tablet. No sedation was recognized.

(4) A third sublingual administration was tried with a lower dose of the sublingual formulation. About 30 mg of a sublingual formulation of riluzole was placed under the tongue of the subject. Once again, acute effects (within 25 minutes) of the sublingual riluzole administration were observed and included the subject feeling relaxed, having a feeling of wellbeing, optimism, and alertness. Similar oral numbness to the previous sublingual administrations was reported but attenuated compared to the oral administration.

Example 2

A 43 year old male administered with riluzole on two occasions.

(1) An oral administration: About 50 mg of an unpulverized riluzole tablet (a formulation not of the invention) was placed on a tongue of the subject. No psychoactive effect was reported but immediately upon application, the subject reported numbness in the local area of application that spread quickly throughout the entire oral cavity. Numbness lasted past 20 minutes. No mood or behavioral sensation was reported. The numbness was intense and bothersome.

(2) A sublingual administration: About 20 mg of a sublingual formulation of riluzole was place under the tongue of the subject for about 30 seconds. Within about 20 minutes, the subject reported the onset of beneficial psychoactive effects including feeling relaxed, calm and less anxious. The subject also reported the sensation of feeling alert. These psychoactive effects or feelings persisted for about 90 minutes. The subject noted that his stomach and gut felt "calm" and previous upset stomach was lessened. The subject reported improved sleep condition that evening.

Within a minute of application, the subject reported that numbness in tongue and mouth reached a peak by about 7 minutes with moderate effect. The numbness started waning significantly after about 18 minutes to very mild by about 24 minutes. The numbness associated with the sublingual administration was noted to be attenuated compared to the oral administration in this subject. Overall, the numbness was very mild and not bothersome with good mouth palatability compared to the pulverized standard riluzole (which was intense, bothersome, generalized and with poor mouth palatability).

Example 3

A 50 year old male was administered with a sublingual formulation of riluzole.

About 5 mg sublingual formulation of riluzole was placed under the tongue of the subject for about 20 seconds until the formulation was fully dissolved. Again, as in the other subjects who received the sublingual administration, there were previously unexpected psychotropic effects soon after administration. Within 20 to 30 minutes, the subject reported the onset of beneficial psychoactive effects and he reported a feeling of relaxation and calm.

After about 7 minutes of administration, the subject reported numbness on the roof of his mouth and tongue that peaked around about 7 minutes, and then was completely gone after about 21 minutes.

Example 4

A 57 year old male was administered with a sublingual formulation of riluzole.

About 70 mg sublingual formulation of riluzole was placed under the tongue of the subject for about 74 seconds. Within about 24 minutes, the subject reported psychoactive effects that were characterized by a feeling of being relaxed and alert that endured through about an hour. The subject reported that he felt so relaxed that he took a restful nap. The subject also reported that his stomach felt relaxed.

After 2 minutes of administration, the subject reported feelings of numbness on the tongue. Peak of mouth numbness occurred after about 4 minutes and numbness waned to mild level after about 15 minutes. Again, compared to the subjects who received oral administration of riluzole, the sublingual administration was associated with an attenuated oral numbness and parathesias.

Example 5

A number of different but related formulations of riluzole for sublingual administration were made. Formulations of 10 mg, 17.5 mg and 35 mg were all made and proved effective at providing the psychoactive effects. The formulations were related in that the same materials were used but the proportions were slightly different.

Each of the formulations included a tablet binder, preferably gelatin; a bulking agent such as mannitol or sorbitol; a solubilizing agent such as docusate sodium; a flavoring agent providing a flavoring such as mint, spearmint, orange, cherry or the like; a sweetener such as sucralose; and purified or distilled water as a solvent. The flavoring agent and the sweetener a merely for taste purposes and can be omitted. To process the tablets, the tablet binder, bulking agent, solubilizing agent, and any sweetener and flavoring are mixed together and solubilized with purified water. The tablet binder should be about 1-10% of the weight of the mixture (including the riluzole and water), preferably 3-5%, most preferably 4-4.5%; the bulking agent should be about 24%, preferably about 3% of the mixture; the solubilizing agent should be about 0.01-0.5% of the mixture, preferably about 0.1-0.2% of the mixture; the flavoring agent (if used) should be about 0.1-1.0%, preferably about 0.3-0.5% of the mixture; and the sweetener (if used) should be about 0.1-1.0% of the mixture, preferably about 0.5% of the mixture. The riluzole should be about 5-25% of the mixture, preferably about 5-20%, more preferably 7-18% of the mixture. The riluzole is milled separately so that the $D_{50}$ particle size is preferably below 2 microns, then it is added to the other solubilized materials. The amount of riluzole is normally a lower percentage for smaller doses than in the higher doses. The remainder of the mixture is purified or deionized water. All of the weights are before lyophillization, where most of the water is removed. Lyophillization is carried out by flash freezing then freeze drying the resulting mixture in tablet form.

Example 6

In this example, the three sublingual formulations of riluzole described in Example 5 were tested for pharmokinetic properties against a commercially available 50 mg riluzole tablet. Partial AUC values, $AUC_{0-0.5}$, $AUC_{0-1}$, $AUC_{0-2}$, and $AUC_{0-12}$ (being AUC values measured for 0.5 hours, 1 hour, 2 hours and 12 hours after the dose was given) were measured and the ratios of the values for the test materials to the 50 mg oral dose were determined. As can be seen from the Table, the values from the sublingual formulation were higher than a weight adjusted value of the oral dosage for all the doses, particularly at the earlier times. The predicted ratios (assuming that the sublingual and oral formulation reached the circulation at the same rate) would be 20% for the 10 mg version, 35% for the 17.5 mg version, and 70% for the 35 mg version.

| Parameter | Treatment Comparison | Ratio |
|---|---|---|
| $AUC_{0-0.5}$ | 10 mg sublingual v. 50 mg oral | 36.19% |
| | 17.5 mg sublingual v. 50 mg oral | 82.16% |
| | 35 mg sublingual v. 50 mgoral | 180.84% |
| $AUC_{0-1}$ | 10 mg sublingual v. 50 mg oral | 29.93% |
| | 17.5 mg sublingual v. 50 mg oral | 65.26% |
| | 35 mg sublingual v. 50 mg oral | 136.20% |
| $AUC_{0-2}$ | 10 mg sublingual v. 50 mg oral | 26.28% |
| | 17.5 mg sublingual v. 50 mg oral | 53.91% |
| | 35 mg sublingual v. 50 mg oral | 110.28% |
| $AUC_{0-12}$ | 10 mg sublingual v. 50 mg oral | 22.47% |
| | 17.5 mg sublingual v. 50 mg oral | 43.38% |
| | 35 mg sublingual v. 50 mg oral | 89.89% |

As is evident from the Table, the sublingual formulations achieved a much higher AUC value than predicted at the earlier times and it is only at 12 hours that the values are near (but still higher) that the weight percent ratios. This shows that the sublingual formulation is being adsorbed and not merely swallowed.

The entire contents of all patents, published patent applications and other references cited herein are hereby expressly incorporated herein in their entireties by reference.

Those skilled in the art will recognize, or be able to ascertain using no more than routine experimentation, numerous equivalents to the specific procedures described herein. Such equivalents are considered to be within the scope of this invention and are covered by the following claims.

APPENDIX A

| ICD-9-CM | ICD-10-CH | Disorder, condition, or problem |
|---|---|---|
| V62.3 | Z55.9 | Academic or educational problem |
| V62.4 | Z60.3 | Acculturation difficulty |
| 308.3 | F43.0 | Acute stress disorder |
| | | Adjustment disorders |
| 309.24 | F43.22 | With anxiety |
| 309.0 | F43.21 | With depressed mood |
| 309.3 | F43.24 | With disturbance of conduct |
| 309.28 | F43.23 | With mixed anxiety and depressed mood |
| 309.4 | F43.25 | With mixed disturbance of emotions and conduct |
| 309.9 | F43.20 | Unspecified |
| V71.01 | Z72.811 | Adult antisocial behavior |
| 307.0 | F98.5 | Adult-onset fluency disorder |
| | | Adult physical abuse by nonspouse or nonpartner, Confirmed |
| 995.81 | T74.11XA | initial encounter |
| 995.81 | T74.11XD | Subsequent encounter |
| | | Adult physical abuse by nonspouse or nonpartner, Suspected |
| 995.81 | T76.11XA | Initial encounter |
| 995.81 | T76.11XD | Subsequent encounter |
| | | Adult psychological abuse by nonspouse or nonpartner, Confirmed |
| 995.82 | T74.31XA | Initial encounter |
| 995.82 | T74.31XD | Subsequent encounter |
| | | Adult psychological abuse by nonspouse or nonpartner, Suspected |
| 995.82 | T76.31XA | Initial encounter |
| 995.82 | T76.31XD | Subsequent encounter |
| | | Adult sexual abuse by nonspouse or nonpartner, Confirmed |
| 995.83 | T74.21XA | Initial encounter |
| 995.83 | T74.21XD | Subsequent encounter |
| | | Adult sexual abuse by nonspouse or nonpartner, Suspected |
| 995.83 | T76.21XA | Initial encounter |
| 995.83 | T76.21XD | Subsequent encounter |

APPENDIX A-continued

| ICD-9-CM | ICD-10-CH | Disorder, condition, or problem |
|---|---|---|
| 300.22 | F40.00 | Agoraphobia |
| 291.89 | | Alcohol-induced anxiety disorder |
| | F10.180 | With mild use disorder |
| | F10.280 | With moderate or severe use disorder |
| | F10.980 | Without use disorder |
| 291.89 | | Alcohol-induced bipolar and related disorder |
| | F10.14 | With mild use disorder |
| | F10.24 | With moderate or severe use disorder |
| | F10.94 | Without use disorder |
| 291.89 | | Alcohol-induced depressive disorder |
| | F10.14 | With mild use disorder |
| | F10.24 | With moderate or severe use disorder |
| | F10.94 | Without use disorder |
| 291.1 | | Alcohol-induced major neurocognitive disorder, Amnestic confabulatory type |
| | F10.26 | With moderate or severe use disorder |
| | F10.96 | Without use disorder |
| 291.2 | | Alcohol-induced major neurocognitive disorder, Nonamnestic confabulatory type |
| | F10.27 | With moderate or severe use disorder |
| | F10.97 | Without use disorder |
| 291.89 | | Alcohol-induced mild neurocognitive disorder |
| | F10.288 | With moderate or severe use disorder |
| | F10.988 | Without use disorder |
| 291.9 | | Alcohol-induced psychotic disorder |
| | F10.159 | With mild use disorder |
| | F10.259 | With moderate or severe use disorder |
| | F10.959 | Without use disorder |
| 291.89 | | Alcohol-induced sexual dysfunction |
| | F10.181 | With mild use disorder |
| | F10.281 | With moderate or severe use disorder |
| | F10.981 | Without use disorder |
| 291.82 | | Alcohol-induced sleep disorder |
| | F10.182 | With mild use disorder |
| | F10.282 | With moderate or severe use disorder |
| | F10.982 | Without use disorder |
| 303.00 | | Alcohol intoxication |
| | F10.129 | With mild use disorder |
| | F10.229 | With moderate or severe use disorder |
| | F10.929 | Without use disorder |
| 291.0 | | Alcohol intoxication delirium |
| | F10.121 | With mild use disorder |
| | F10.221 | With moderate or severe use disorder |
| | F10.921 | Without use disorder |
| | | Alcohol use disorder |
| 305.00 | F10.10 | Mild |
| 303.90 | F10.20 | Moderate |
| 303.90 | F10.20 | Severe |
| 291.81 | | Alcohol withdrawal |
| | F10.232 | With perceptual disturbances |
| | F10.239 | Without perceptual disturbances |
| 291.0 | F10.231 | Alcohol withdrawal delirium |
| 292.89 | | Amphetamine (or other stimulant)-induced anxiety disorder |
| | F15.180 | With mild use disorder |
| | F15.280 | With moderate or severe use disorder |
| | F15.980 | Without use disorder |
| 292.84 | | Amphetamine (or other stimulant)-induced bipolar and related disorder |
| | F15.14 | With mild use disorder |
| | F15.24 | With moderate or severe use disorder |
| | F15.94 | Without use disorder |
| | F15.921 | Amphetamine (or other stimulant)-induced delirium |
| 292.84 | | Amphetamine (or other stimulant)-induced depressive disorder |
| | F15.14 | With mild use disorder |
| | F15.24 | With moderate or severe use disorder |
| | F15.94 | Without use disorder |
| 292.89 | | Amphetamine (or other stimulant)-induced obsessive-compulsive and related disorder |
| | F15.188 | With mild use disorder |
| | F15.288 | With moderate or severe use disorder |
| | F15.988 | Without use disorder |
| 292.9 | | Amphetamine (or other stimulant)-induced psychotic disorder |
| | F15.159 | With mild use disorder |
| | F15.259 | With moderate or severe use disorder |
| | F15.959 | Without use disorder |

APPENDIX A-continued

| ICD-9-CM | ICD-10-CH | Disorder, condition, or problem |
|---|---|---|
| 292.89 | | Amphetamine (or other stimulant)-induced sexual dysfunction |
| | F15.181 | With mild use disorder |
| | F15.281 | With moderate or severe use disorder |
| | F15.981 | Without use disorder |
| 292.85 | | Amphetamine (or other stimulant)-induced sleep disorder |
| | F15.182 | With mild use disorder |
| | F15.282 | With moderate or severe use disorder |
| | F15.982 | Without use disorder |
| 292.89 | | Amphetamine or other stimulant intoxication |
| | | Amphetamine or other stimulant intoxication, With perceptual disturbances |
| | F15.122 | With mild use disorder |
| | F15.222 | With moderate or severe use disorder |
| | F15.922 | Without use disorder |
| | | Amphetamine or other stimulant intoxication, Without perceptual disturbances |
| | F15.129 | With mild use disorder |
| | F15.229 | With moderate or severe use disorder |
| | F15.929 | Without use disorder |
| 292.81 | | Amphetamine (or other stimulant) intoxication delirium |
| | F15.121 | With mild use disorder |
| | F15.221 | With moderate or severe use disorder |
| | F15.921 | Without use disorder |
| 292.0 | F15.23 | Amphetamine or other stimulant withdrawal |
| | | Amphetamine-type substance use disorder |
| 305.70 | F15.10 | Mild |
| 304.40 | F15.20 | Moderate |
| 304.40 | F15.20 | Severe |
| 307.1 | | Anorexia nervosa |
| | F50.02 | Binge-eating/purging type |
| | F50.01 | Restricting type |
| | | Antidepressant discontinuation syndrome |
| 995.29 | T43.205A | Initial encounter |
| 995.29 | T43.205S | Sequelae |
| 995.29 | T43.205D | Subsequent encounter |
| 301.7 | F60.2 | Antisocial personality disorder |
| 293.84 | F06.4 | Anxiety disorder due to another medical condition |
| | | Attention-deficit/hyperactivity disorder |
| 314.01 | F90.2 | Combined presentation |
| 314.01 | F90.1 | Predominantly hyperactive/impulsive presentation |
| 314.00 | F90.0 | Predominantly inattentive presentation |
| 299.00 | F84.0 | Autism spectrum disorder |
| 301.82 | F60.6 | Avoidant personality disorder |
| 307.59 | F50.8 | Avoidant/restrictive food intake disorder |
| 307.51 | F50.8 | Binge-eating disorder |
| | | Bipolar I disorder, Current or most recent episode depressed |
| 296.56 | F31.76 | In full remission |
| 296.55 | F31.75 | In partial remission |
| 296.51 | F31.31 | Mild |
| 296.52 | F31.32 | Moderate |
| 296.53 | F31.4 | Severe |
| 296.54 | F31.5 | With psychotic features |
| 296.50 | F31.9 | Unspecified |
| 296.40 | F31.0 | Bipolar I disorder, Current or most recent episode hypomanic |
| 296.46 | F31.72 | In full remission |
| 296.45 | F31.71 | In partial remission |
| 296.40 | F31.9 | Unspecified |
| | | Bipolar I disorder, Current or most recent episode manic |
| 296.46 | F31.74 | In full remission |
| 296.45 | F31.73 | In partial remission |
| 296.41 | F31.11 | Mild |
| 296.42 | F31.12 | Moderate |
| 296.43 | F31.13 | Severe |
| 296.44 | F31.2 | With psychotic features |
| 296.40 | F31.9 | Unspecified |
| 296.7 | F31.9 | Bipolar I disorder, Current or most recent episode unspecified |
| 296.89 | F31.81 | Bipolar II disorder |
| 293.83 | | Bipolar and related disorder due to another medical condition |
| | F06.33 | With manic features |
| | F06.33 | With manic- or hypomanic-like episodes |
| | F06.34 | With mixed features |
| 300.7 | F45.22 | Body dysmorphic disorder |
| V62.89 | R41.83 | Borderline intellectual functioning |
| 301.83 | F60.3 | Borderline personality disorder |
| 298.8 | F23 | Brief psychotic disorder |

APPENDIX A-continued

| ICD-9-CM | ICD-10-CH | Disorder, condition, or problem |
|---|---|---|
| 307.51 | F50.2 | Bulimia nervosa |
| 292.89 | | Caffeine-induced anxiety disorder |
| | F15.180 | With mild use disorder |
| | F15.280 | With moderate or severe use disorder |
| | F15.980 | Without use disorder |
| 292.85 | | Caffeine-induced sleep disorder |
| | F15.182 | With mild use disorder |
| | F15.282 | With moderate or severe use disorder |
| | F15.982 | Without use disorder |
| 305.90 | F15.929 | Caffeine intoxication |
| 292.0 | F15.93 | Caffeine withdrawal |
| 292.89 | | *Cannabis*-induced anxiety disorder |
| | F12.180 | With mild use disorder |
| | F12.280 | With moderate or severe use disorder |
| | F12.980 | Without use disorder |
| 292.9 | | *Cannabis*-induced psychotic disorder |
| | F12.159 | With mild use disorder |
| | F12.259 | With moderate or severe use disorder |
| | F12.959 | Without use disorder |
| 292.85 | | *Cannabis*-induced sleep disorder |
| | F12.188 | With mild use disorder |
| | F12.288 | With moderate or severe use disorder |
| | F12.988 | Without use disorder |
| 292.89 | | *Cannabis* intoxication |
| | | *Cannabis* intoxication, With perceptual disturbances |
| | F12.122 | With mild use disorder |
| | F12.222 | With moderate or severe use disorder |
| | F12.922 | Without use disorder |
| | | *Cannabis* intoxication, Without perceptual disturbances |
| | F12.129 | With mild use disorder |
| | F12.229 | With moderate or severe use disorder |
| | F12.929 | Without use disorder |
| 292.81 | | *Cannabis* intoxication delirium |
| | F12.121 | With mild use disorder |
| | F12.221 | With moderate or severe use disorder |
| | F12.921 | Without use disorder |
| | | *Cannabis* use disorder |
| 305.20 | F12.10 | Mild |
| 304.30 | F12.20 | Moderate |
| 304.30 | F12.20 | Severe |
| 292.0 | F12.288 | *Cannabis* withdrawal |
| 293.89 | F06.1 | Catatonia associated with another mental disorder (catatonia specifier) |
| 293.89 | F06.1 | Catatonic disorder due to another medical condition |
| | | Central sleep apnea |
| 780.57 | G47.37 | Central sleep apnea comorbid with opioid use |
| 786.04 | R06.3 | Cheyne-Stokes breathing |
| 327.21 | G47.31 | Idiopathic central sleep apnea |
| V61.29 | Z62.898 | Child affected by parental relationship distress |
| | | Child neglect, Confirmed |
| 995.52 | T74.02XA | Initial encounter |
| 995.52 | T74.02XD | Subsequent encounter |
| | | Child neglect, Suspected |
| 995.52 | T76.02XA | Initial encounter |
| 995.52 | T76.02XD | Subsequent encounter |
| V71.02 | Z72.810 | Child or adolescent antisocial behavior |
| | | Child physical abuse, Confirmed |
| 995.54 | T74.12XA | Initial encounter |
| 995.54 | T74.12XD | Subsequent encounter |
| | | Child physical abuse, Suspected |
| 995.54 | T76.12XA | Initial encounter |
| 995.54 | T76.12XD | Subsequent encounter |
| | | Child psychological abuse, Confirmed |
| 995.51 | T74.32XA | Initial encounter |
| 995.51 | T74.32XD | Subsequent encounter |
| | | Child psychological abuse, Suspected |
| 995.51 | T76.32XA | Initial encounter |
| 995.51 | T76.32XD | Subsequent encounter |
| | | Child sexual abuse, Confirmed |
| 995.53 | T74.22XA | Initial encounter |
| 995.53 | T74.22XD | Subsequent encounter |
| | | Child sexual abuse, Suspected |
| 995.53 | T76.22XA | Initial encounter |
| 995.53 | T76.22XD | Subsequent encounter |
| 315.35 | F80.81 | Childhood-onset fluency disorder (stuttering) |
| | | Circadian rhythm sleep-wake disorders |
| 307.45 | G47.22 | Advanced sleep phase type |

APPENDIX A-continued

| ICD-9-CM | ICD-10-CH | Disorder, condition, or problem |
|---|---|---|
| 307.45 | G47.21 | Delayed sleep phase type |
| 307.45 | G47.23 | irregular sleep-wake type |
| 307.45 | G47.24 | Non-24-hour sleep-wake type |
| 307.45 | G47.26 | Shift work type |
| 307.45 | G47.20 | Unspecified type |
| 292.89 | | Cocaine-induced anxiety disorder |
| | F14.180 | With mild use disorder |
| | F14.280 | With moderate or severe use disorder |
| | F14.980 | Without use disorder |
| 292.84 | | Cocaine-induced bipolar and related disorder |
| | F14.14 | With mild use disorder |
| | F14.24 | With moderate or severe use disorder |
| | F14.94 | Without use disorder |
| 292.84 | | Cocaine-induced depressive disorder |
| | F14.14 | With mild use disorder |
| | F14.24 | With moderate or severe use disorder |
| | F14.94 | Without use disorder |
| 292.89 | | Cocaine-induced obsessive-compulsive and related disorder |
| | F14.188 | With mild use disorder |
| | F14.288 | With moderate or severe use disorder |
| | F14.988 | Without use disorder |
| 292.9 | | Cocaine-induced psychotic disorder |
| | F14.159 | With mild use disorder |
| | F14.259 | With moderate or severe use disorder |
| | F14.959 | Without use disorder |
| 292.39 | | Cocaine-Induced sexual dysfunction |
| | F14.181 | With mild use disorder |
| | F14.281 | With moderate or severe use disorder |
| | F14.981 | Without use disorder |
| 292.85 | | Cocaine-induced sleep disorder |
| | F14.182 | With mild use disorder |
| | F14.282 | With moderate or severe use disorder |
| | F14.982 | Without use disorder |
| 292.89 | | Cocaine intoxication |
| | | Cocaine intoxication, With perceptual disturbances |
| | F14.122 | With mild use disorder |
| | F14.222 | With moderate or severe use disorder |
| | F14.922 | Without use disorder |
| | | Cocaine intoxication, Without perceptual disturbances |
| | F14.129 | With mild use disorder |
| | F14.229 | With moderate or severe use disorder |
| | F14.929 | Without use disorder |
| 292.81 | | Cocaine intoxication delirium |
| | F14.121 | With mild use disorder |
| | F14.221 | With moderate or severe use disorder |
| | F14.921 | Without use disorder |
| | | Cocaine use disorder |
| 305.60 | F14.10 | Mild |
| 304.20 | F14.20 | Moderate |
| 304.20 | F14.20 | Severe |
| 292.0 | F14.23 | Cocaine withdrawal |
| | | Conduct disorder |
| 312.82 | F91.2 | Adolescent-onset type |
| 312.81 | F91.1 | Childhood-onset type |
| 312.89 | F91.9 | Unspecified onset |
| 300.11 | | Conversion disorder (functional neurological symptom disorder) |
| | F44.4 | With abnormal movement |
| | F44.6 | With anesthesia or sensory loss |
| | F44.5 | With attacks or seizures |
| | F44.7 | With mixed symptoms |
| | F44.6 | With special sensory symptoms |
| | F44.4 | With speech symptoms |
| | F44.4 | With swallowing symptoms |
| | F44.4 | With weakness/paralysis |
| V62.5 | Z65.0 | Conviction in civil or criminal proceedings without imprisonment |
| 301.13 | F34.0 | Cyclothymic disorder |
| 302.74 | F52.32 | Delayed ejaculation |
| | | Delirium |
| 293.0 | F05 | Delirium due to another medical condition |
| 293.0 | F05 | Delirium due to multiple etiologies |
| 292.81 | | Medication-induced delirium (for ICD-10-CM codes, see specific substances) |
| | | Substance intoxication delirium (see specific substances for codes) |
| | | Substance withdrawal delirium (see specific substances for codes) |

APPENDIX A-continued

| ICD-9-CM | ICD-10-CH | Disorder, condition, or problem |
|---|---|---|
| 297.1 | F22 | Delusional disorder |
| 301.6 | F60.7 | Dependent personality disorder |
| 300.6 | F48.1 | Depersonalization/derealization disorder |
| 293.83 | | Depressive disorder due to another medical condition |
| | F06.31 | With depressive features |
| | F06.32 | With major depressive-like episode |
| | F06.34 | With mixed features |
| 315.4 | F82 | Developmental coordination disorder |
| V60.89 | Z59.2 | Discord with neighbor, lodger, or landlord |
| V62.89 | Z64.4 | Discord with social service provider, including probation officer, case manager, or social services worker |
| 313.89 | F94.2 | Disinhibited social engagement disorder |
| V61.03 | Z63.5 | Disruption of family by separation or divorce |
| 296.99 | F34.8 | Disruptive mood dysregulation disorder |
| 300.12 | F44.0 | Dissociative amnesia |
| 300.13 | F44.1 | Dissociative amnesia, with dissociative fugue |
| 300.14 | F44.81 | Dissociative identity disorder |
| 307.7 | F98.1 | Encopresis |
| 307.6 | F98.0 | Enuresis |
| 302.72 | F52.21 | Erectile disorder |
| 698.4 | L98.1 | Excoriation (skin-picking) disorder |
| 302.4 | F65.2 | Exhibitionistic disorder |
| V62.22 | Z65.5 | Exposure to disaster, war, or other hostilities |
| V60.2 | Z59.5 | Extreme poverty |
| 300.19 | F68.10 | Factitious disorder |
| 302.73 | F52.31 | Female orgasmic disorder |
| 302.72 | F52.22 | Female sexual interest/arousal disorder |
| 302.81 | F65.0 | Fetishistic disorder |
| 302.89 | F65.81 | Frotteuristic disorder |
| 312.31 | F63.0 | Gambling disorder |
| 302.85 | F64.1 | Gender dysphoria in adolescents and adults |
| 302.6 | F64.2 | Gender dysphoria in children |
| 300.02 | F41.1 | Generalized anxiety disorder |
| 302.76 | F52.6 | Genito-pelvic pain/penetration disorder |
| 315.8 | F88 | Global developmental delay |
| 292.89 | F16.983 | Hallucinogen persisting perception disorder |
| V61.8 | Z63.8 | High expressed emotion level within family |
| 301.50 | F60.4 | Histrionic personality disorder |
| 300.3 | F42 | Hoarding disorder |
| V60.0 | Z59.0 | Homelessness |
| 307.44 | F51.11 | Hypersomnolence disorder |
| 300.7 | F45.21 | Illness anxiety disorder |
| V62.5 | Z65.1 | Imprisonment or other incarceration |
| V60.1 | Z59.1 | Inadequate housing |
| 292.89 | | Inhalant-induced anxiety disorder |
| | F18.180 | With mild use disorder |
| | F18.280 | With moderate or severe use disorder |
| | F18.980 | Without use disorder |
| 292.84 | | Inhalant-induced depressive disorder |
| | F18.14 | With mild use disorder |
| | F18.24 | With moderate or severe use disorder |
| | F18.94 | Without use disorder |
| 292.82 | | Inhalant-induced major neurocognitive disorder |
| | F18.17 | With mild use disorder |
| | F18.27 | With moderate or severe use disorder |
| | F18.97 | Without use disorder |
| 292.89 | | Inhalant-induced mild neurocognitive disorder |
| | F18.188 | With mild use disorder |
| | F18.288 | With moderate or severe use disorder |
| | F18.988 | Without use disorder |
| 292.9 | | Inhalant-induced psychotic disorder |
| | F18.159 | With mild use disorder |
| | F18.259 | With moderate or severe use disorder |
| | F18.959 | Without use disorder |
| 292.89 | | Inhalant intoxication |
| | F18.129 | With mild use disorder |
| | F18.229 | With moderate or severe use disorder |
| | F18.929 | Without use disorder |
| 292.81 | | Inhalant intoxication delirium |
| | F18.121 | With mild use disorder |
| | F18.221 | With moderate or severe use disorder |
| | F18.921 | Without use disorder |
| | | Inhalant use disorder |
| 305.90 | F13.10 | Mild |
| 304.60 | F18.20 | Moderate |
| 304.60 | F18.20 | Severe |
| 307.42 | F51.01 | Insomnia disorder |

APPENDIX A-continued

| ICD-9-CM | ICD-10-CH | Disorder, condition, or problem |
|---|---|---|
| V60.2 | Z59.7 | Insufficient social insurance or welfare support |
| | | Intellectual disability (Intellectual developmental disorder) |
| 317 | F70 | Mild |
| 318.0 | F71 | Moderate |
| 318.1 | F72 | Severe |
| 318.2 | F73 | Profound |
| 312.34 | F63.81 | Intermittent explosive disorder |
| 312.32 | F63.2 | Kleptomania |
| V60.2 | Z59.4 | Lack of adequate food or safe drinking water |
| 315.32 | F80.2 | Language disorder |
| V60.2 | Z59.6 | Low income |
| | | Major depressive disorder, Recurrent episode |
| 296.36 | F33.42 | In full remission |
| 296.35 | F33.41 | In partial remission |
| 296.31 | F33.0 | Mild |
| 296.32 | F33.1 | Moderate |
| 296.33 | F33.2 | Severe |
| 296.34 | F33.3 | With psychotic features |
| 296.30 | F33.9 | Unspecified |
| | | Major depressive disorder, Single episode |
| 296.26 | F32.5 | In full remission |
| 296.25 | F32.4 | In partial remission |
| 296.21 | F32.0 | Mild |
| 296.22 | F32.1 | Moderate |
| 296.23 | F32.2 | Severe |
| 296.24 | F32.3 | With psychotic features |
| 296.20 | F32.9 | Unspecifed |
| 331.9 | G31.9 | Major frontotemporal neurocognitive disorder, Possible |
| | | Major frontotemporal neurocognitive disorder, Probable (code first 331.19 [G31.09] frontotemporal disease) |
| 294.11 | F02.81 | With behavioral disturbance |
| 294.10 | F02.80 | Without behavioral disturbance |
| 331.9 | G31.9 | Major neurocognitlve disorder due to Alzheimer's disease, Possible |
| | | Major neurocognitlve disorder due to Alzheimer's disease, Probable (code first 331.0 [G30.9] Alzheimer's disease) |
| 294.11 | F02.81 | With behavioral disturbance |
| 294.10 | F02.80 | Without behavioral disturbance |
| | | Major neurocognitive disorder due to another medical condition |
| 294.11 | F02.81 | With behavioral disturbance |
| 294.10 | F02.80 | Without behavioral disturbance |
| | | Major neurocognitlve disorder due to HIV Infection (code first 042 [B20] HIV infection) |
| 294.11 | F02.81 | With behavioral disturbance |
| 294.10 | F02.80 | Without behavioral disturbance |
| | | Major neurocognitive disorder due to Huntington's disease (code first 333.4 [G10] Huntington's disease) |
| 294.11 | F02.81 | With behavioral disturbance |
| 294.10 | F02.80 | Without behavioral disturbance |
| 331.9 | G31.9 | Major neurocognitive disorder with Lewy bodies, Possible |
| | | Major neurocognitive disorder with Lewy bodies, Probable (code first 331.82 [G31.83] Lewy body disease) |
| 294.11 | F02.81 | With behavioral disturbance |
| 294.10 | F02.80 | Without behavioral disturbance |
| | | Major neurocognitive disorder due to multiple etiologies |
| 294.11 | F02.81 | With behavioral disturbance |
| 294.10 | F02.80 | Without behavioral disturbance |
| 331.9 | G31.9 | Major neurocognitive disorder due to Parkinson's disease, Possible |
| | | Major neurocognitive disorder due to Parkinson's disease, Probable (code first 332.0 [G20] Parkinson's disease) |
| 294.11 | F02.81 | With behavioral disturbance |
| 294.10 | F02.80 | Without behavioral disturbance |
| | | Major neurocognitive disorder due to prion disease (code first 046.79 [A81.9] prion disease) |
| 294.11 | F02.81 | With behavioral disturbance |
| 294.10 | F02.80 | Without behavioral disturbance |
| | | Major neurocognitive disorder due to traumatic brain injury (code first 907.0 late effect of intracranial injury without skull fracture [S06.2X9S diffuse traumatic brain injury with loss of consciousness of unspecified duration, sequela]) |
| 294.11 | F02.81 | With behavioral disturbance |
| 294.10 | F02.80 | Without behavioral disturbance |
| 331.9 | G31.9 | Major vascular neurocognitive disorder, Possible |
| | | Major vascular neurocognitive disorder, Probable |
| 290.40 | F01.51 | With behavioral disturbance |
| 290.40 | F01.50 | Without behavioral disturbance |

APPENDIX A-continued

| ICD-9-CM | ICD-10-CH | Disorder, condition, or problem |
|---|---|---|
| 302.71 | F52.0 | Male hypoactive sexual desire disorder |
| V65.2 | Z76.5 | Malingering |
| 333.99 | G25.71 | Medication-induced acute akathisia |
| 333.72 | G24.02 | Medication-induced acute dystonia |
| 292.81 | | Medication-induced delirium (for ICD-10-CM codes, see specific substances) |
| 333.1 | G25.1 | Medication-induced postural tremor |
| 331.83 | G31.84 | Mild frontotemporal neurocognitive disorder |
| 331.83 | G31.84 | Mild neurocognitive disorder due to Alzheimer's disease |
| 331.83 | G31.84 | Mild neurocognitive disorder due to another medical condition |
| 331.83 | G31.S4 | Mild neurocognitive disorder due to HIV infection |
| 331.83 | G31.84 | Mild neurocognitive disorder due to Huntington's disease |
| 331.83 | G31.84 | Mild neurocognitive disorder due to multiple etiologies |
| 331.83 | G31.84 | Mild neurocognitive disorder due to Parkinson's disease |
| 331.83 | G31.84 | Mild neurocognitive disorder due to prion disease |
| 331.83 | G31.84 | Mild neurocognitive disorder due to traumatic brain injury |
| 331.83 | G31.84 | Mild neurocognitive disorder with Lewy bodies |
| 331.83 | G31.84 | Mild vascular neurocognitive disorder |
| 301.81 | F60.81 | Narcissistic personality disorder |
| | | Narcolepsy |
| 347.00 | G47.419 | Autosomal dominant cerebellar ataxia, deafness, and narcolepsy |
| 347.00 | G47.419 | Autosomal dominant narcolepsy, obesity, and type 2 diabetes |
| 347.10 | G47.429 | Narcolepsy secondary to another medical condition |
| 347.01 | G47.411 | Narcolepsy with cataplexy but without hypocretin deficiency |
| 347.00 | G47.419 | Narcolepsy without cataplexy but with hypocretin deficiency |
| 332.1 | G21.11 | Neuroleptic-Induced parkinsonism |
| 333.92 | G21.0 | Neuroleptic malignant syndrome |
| 307.47 | F51.5 | Nightmare disorder |
| V15.81 | Z91.19 | Nonadherence to medical treatment |
| | | Non-rapid eye movement sleep arousal disorders |
| 307.46 | F51.4 | Sleep terror type |
| 307.46 | F51.3 | Sleepwalking type |
| 300.3 | F42 | Obsessive-compulsive disorder |
| 301.4 | F60.5 | Obsessive-compulsive personality disorder |
| 294.8 | F06.8 | Obsessive-compulsive and related disorder due to another medical condition |
| 327.23 | G47.33 | Obstructive sleep apnea hypopnea |
| 292.89 | | Opioid-induced anxiety disorder |
| | F11.188 | With mild use disorder |
| | F11.288 | With moderate or severe use disorder |
| | F11.988 | Without use disorder |
| | F11.921 | Opioid-induced delirium |
| 292.84 | | Opioid-induced depressive disorder |
| | F11.14 | With mild use disorder |
| | F11.24 | With moderate or severe use disorder |
| | F11.94 | Without use disorder |
| 292.89 | | Opioid-induced sexual dysfunction |
| | F11.181 | With mild use disorder |
| | F11.281 | With moderate or severe use disorder |
| | F11.981 | Without use disorder |
| 292.85 | | Opioid-induced sleep disorder |
| | F11.182 | With mild use disorder |
| | F11.282 | With moderate or severe use disorder |
| | F11.982 | Without use disorder |
| 292.89 | | Opioid intoxication |
| | | Opioid intoxication, With perceptual disturbances |
| | F11.122 | With mild use disorder |
| | F11.222 | With moderate or severe use disorder |
| | F11.922 | Without use disorder |
| | | Opioid intoxication, Without perceptual disturbances |
| | F11.129 | With mild use disorder |
| | F11.229 | With moderate or severe use disorder |
| | F11.929 | Without use disorder |
| 292.81 | | Opioid intoxication delirium |
| | F11.121 | With mild use disorder |
| | F11.221 | With moderate or severe use disorder |
| | F11.921 | Without use disorder |
| | | Opioid use disorder |
| 305.50 | F11.10 | Mild |
| 304.00 | F11.20 | Moderate |
| 304.00 | F11.20 | Severe |
| 292.0 | F11.23 | Opioid withdrawal |
| 292.0 | F11.23 | Opioid withdrawal delirium |
| 313.81 | F91.3 | Oppositional defiant disorder |
| | | Other adverse effect of medication |

APPENDIX A-continued

| ICD-9-CM | ICD-10-CH | Disorder, condition, or problem |
|---|---|---|
| 995.20 | T50.905A | initial encounter |
| 995.20 | T50.905S | Sequelae |
| 995.20 | TS0.905D | Subsequent encounter |
| | | Other circumstances related to adult abuse by nonspouse or nonpartner |
| V62.83 | Z69.82 | Encounter for mental health services for perpetrator of nonspousal adult abuse |
| V65.49 | Z69.81 | Encounter for mental health services for victim of nonspousal adult abuse |
| | | Other circumstances related to child neglect |
| V62.83 | Z69.021 | Encounter for mental health services for perpetrator of nonparental child neglect |
| V61.22 | Z69.011 | Encounter for mental health services for perpetrator of parental child neglect |
| V61.21 | Z69.010 | Encounter for mental health services for victim of child neglect by parent |
| V61.21 | Z69.020 | Encounter for mental health services for victim of nonparental child neglect |
| V15.42 | Z62.812 | Personal history (past history) of neglect in childhood |
| | | Other circumstances related to child physical abuse |
| V62.83 | Z69.021 | Encounter for mental health services for perpetrator of nonparental child abuse |
| V61.22 | Z69.011 | Encounter for mental health services for perpetrator of parental child abuse |
| V61.21 | Z69.010 | Encounter for mental health services for victim of child abuse by parent |
| V61.21 | Z69.020 | Encounter for mental health services for victim of nonparental child abuse |
| V15.41 | Z62.810 | Personal history (past history) of physical abuse in childhood |
| | | Other circumstances related to child psychological abuse |
| V62.83 | Z69.021 | Encounter for mental health services for perpetrator of nonparental child psychological abuse |
| V61.22 | Z69.011 | Encounter for mental health services for perpetrator of parental child psychological abuse |
| V61.21 | Z69.010 | Encounter for mental health services for victim of child psychological abuse by parent |
| V61.21 | Z69.020 | Encounter for mental health services for victim of nonparental child psychological abuse |
| V15.42 | Z62.811 | Personal history (past history) of psychological abuse in childhood |
| | | Other circumstances related to child sexual abuse |
| V62.83 | Z69.021 | Encounter for mental health services for perpetrator of nonparental child sexual abuse |
| V61.22 | Z69.011 | Encounter for mental health services for perpetrator of parental child sexual abuse |
| V61.21 | Z69.010 | Encounter for mental health services for victim of child sexual abuse by parent |
| V61.21 | Z69.020 | Encounter for mental health services for victim of nonparental child sexual abuse |
| V15.41 | Z62.810 | Personal history (past history) of sexual abuse in childhood |
| | | Other circumstances related to spouse or partner abuse, Psychological |
| V61.12 | Z69.12 | Encounter for mental health services for perpetrator of spouse or partner psychological abuse |
| V61.11 | Z69.11 | Encounter for mental health services for victim of spouse or partner psychological abuse |
| V15.42 | Z91.411 | Personal history (past history) of spouse or partner psychological abuse |
| | | Other circumstances related to spouse or partner neglect |
| V61.12 | Z69.12 | Encounter for mental health services for perpetrator of spouse or partner neglect |
| V61.11 | Z69.11 | Encounter for mental health services for victim of spouse or partner neglect |
| V15.42 | Z91.412 | Personal history (past history) of spouse or partner neglect |
| | | Other circumstances related to spouse or partner violence, Physical |
| V61.12 | Z69.12 | Encounter for mental health services for perpetrator of spouse or partner violence, Physical |
| V61.11 | Z69.11 | Encounter for mental health services for victim of spouse or partner violence, Physical |
| V15.41 | Z91.410 | Personal history (past history) of spouse or partner violence, Physical |
| | | Other circumstances related to spouse or partner violence, Sexual |
| V61.12 | Z69.12 | Encounter for mental health services for perpetrator of spouse or partner violence, Sexual |

APPENDIX A-continued

| ICD-9-CM | ICD-10-CH | Disorder, condition, or problem |
|---|---|---|
| V61.11 | Z69.81 | Encounter for mental health services for victim of spouse or partner violence, Sexual |
| V15.41 | Z91.410 | Personal history (past history) of spouse or partner violence, Sexual |
| V65.40 | Z71.9 | Other counseling or consultation |
| 292.89 | | Other hallucinogen-induced anxiety disorder |
| | F16.180 | With mild use disorder |
| | F16.280 | With moderate or severe use disorder |
| | F16.980 | Without use disorder |
| 292.84 | | Other hallucinogen-induced bipolar and related disorder |
| | F16.14 | With mild use disorder |
| | F16.24 | With moderate or severe use disorder |
| | F16.94 | Without use disorder |
| 292.84 | | Other hallucinogen-induced depressive disorder |
| | F16.14 | With mild use disorder |
| | F16.24 | With moderate or severe use disorder |
| | F16.94 | Without use disorder |
| 292.9 | | Other hallucinogen-induced psychotic disorder |
| | F16.159 | With mild use disorder |
| | F16.259 | With moderate or severe use disorder |
| | F16.959 | Without use disorder |
| 292.89 | | Other hallucinogen intoxication |
| | F16.129 | With mild use disorder |
| | F16.229 | With moderate or severe use disorder |
| | F16.929 | Without use disorder |
| 292.81 | | Other hallucinogen intoxication delirium |
| | F16.121 | With mild use disorder |
| | F16.221 | With moderate or severe use disorder |
| | F16.921 | Without use disorder |
| | | Other hallucinogen use disorder |
| 305.30 | F16.10 | Mild |
| 304.50 | F16.20 | Moderate |
| 304.50 | F16.20 | Severe |
| 333.99 | G25.79 | Other medication-induced movement disorder |
| 332.1 | G21.19 | Other medication-induced parkinsonism |
| V15.49 | Z91.49 | Other personal history of psychological trauma |
| V15.89 | Z91.89 | Other personal risk factors |
| V62.29 | Z56.9 | Other problem related to employment |
| V62.89 | Z65.8 | Other problem related to psychosocial circumstances |
| 300.09 | F41.8 | Other specified anxiety disorder |
| 314.01 | F90.8 | Other specified attention-deficit/hyperactivity disorder |
| 296.89 | F31.89 | Other specified bipolar and related disorder |
| 780.09 | R41.0 | Other specified delirium |
| 311 | F32.8 | Other specified depressive disorder |
| 312.89 | F91.8 | Other specified disruptive, impulse-control, and conduct disorder |
| 300.15 | F44.89 | Other specified dissociative disorder |
| | | Other specified elimination disorder |
| 787.60 | R15.9 | With fecal symptoms |
| 738.39 | N39.493 | With urinary symptoms |
| 307.59 | F50.8 | Other specified feeding or eating disorder |
| 302.6 | F64.8 | Other specified gender dyspnoea |
| 780.54 | G47.19 | Other specified hypersomnolence disorder |
| 780.52 | G47.09 | Other specified insomnia disorder |
| 300.9 | F99 | Other specified mental disorder |
| 294.8 | F06.8 | Other specified mental disorder due to another medical condition |
| 315.8 | F88 | Other specified neurodevelopmental disorder |
| 300.3 | F42 | Other specified obsessive-compulsive and related disorder |
| 302.89 | F65.89 | Other specified paraphilic disorder |
| 301.89 | F60.89 | Other specified personality disorder |
| 298.8 | F28 | Other specified schizophrenia spectrum and other psychotic disorder |
| 302.79 | F52.8 | Other specified sexual dysfunction |
| 780.59 | G47.8 | Other specified sleep- wake disorder |
| 300.89 | F45.8 | Other specified somatic symptom and related disorder |
| 307.20 | F95.8 | Other specified tic disorder |
| 309.89 | F43.8 | Other specified trauma- and stressor-related disorder |
| 292.89 | | Other (or unknown) substance-induced anxiety disorder |
| | F19.180 | With mild use disorder |
| | F19.280 | With moderate or severe use disorder |
| | F19.980 | Without use disorder |

APPENDIX A-continued

| ICD-9-CM | ICD-10-CH | Disorder, condition, or problem |
|---|---|---|
| 292.84 | | Other (or unknown) substance-induced bipolar and related disorder |
| | F19.14 | With mild use disorder |
| | F19.24 | With moderate or severe use disorder |
| | F19.94 | Without use disorder |
| | F19.921 | Other (or unknown) substance-induced delirium |
| 292.84 | | Other (or unknown) substance-induced depressive disorder |
| | F19.14 | With mild use disorder |
| | F19.24 | With moderate or severe use disorder |
| | F19.94 | Without use disorder |
| 292.82 | | Other (or unknown) substance-induced major neurocognitive disorder |
| | F19.17 | With mild use disorder |
| | F19.27 | With moderate or severe use disorder |
| | F19.97 | Without use disorder |
| 292.89 | | Other (or unknown) substance-induced mild neurocognitive disorder |
| | F19.188 | With mild use disorder |
| | F19.288 | With moderate or severe use disorder |
| | F19.988 | Without use disorder |
| 292.89 | | Other (or unknown) substance-induced obsessive-compulsive and related disorder |
| | F19.188 | With mild use disorder |
| | F19.288 | With moderate or severe use disorder |
| | F19.988 | Without use disorder |
| 292.9 | | Other (or unknown) substance-induced psychotic disorder |
| | F19.159 | With mild use disorder |
| | F19.259 | With moderate or severe use disorder |
| | F19.959 | Without use disorder |
| 292.89 | | Other (or unknown) substance-induced sexual dysfunction |
| | F19.181 | With mild use disorder |
| | F19.281 | With moderate or severe use disorder |
| | F19.981 | Without use disorder |
| 292.85 | | Other (or unknown) substance-induced sleep disorder |
| | F19.182 | With mild use disorder |
| | F19.282 | With moderate or severe use disorder |
| | F19.982 | Without use disorder |
| 292.89 | | Other (or unknown) substance intoxication |
| | F19.129 | With mild use disorder |
| | F19.229 | With moderate or severe use disorder |
| | F19.929 | Without use disorder |
| 292.81 | | Other (or unknown) substance intoxication delirium |
| | F19.121 | With mild use disorder |
| | F19.221 | With moderate or severe use disorder |
| | F19.921 | Without use disorder |
| | | Other (or unknown) substance use disorder |
| 305.90 | F19.10 | Mild |
| 304.90 | F19.20 | Moderate |
| 304.90 | F19.2.0 | Severe |
| 292.0 | F19.239 | Other (or unknown) substance withdrawal |
| 292.0 | F19.231 | Other (or unknown) substance withdrawal delirium |
| | | Other or unspecified stimulant use disorder |
| 305.70 | F15.10 | Mild |
| 304.40 | F15.20 | Moderate |
| 304.40 | F15.20 | Severe |
| 278.00 | E66.9 | Overweight or obesity |
| | | Panic attack specifier |
| 300.01 | F41.0 | Panic disorder |
| 301.0 | F60.0 | Paranoid personality disorder |
| V61.20 | Z62.820 | Parent-child relational problem |
| 302.2 | F65.4 | Pedophilic disorder |
| 307.22 | F95.1 | Persistent (chronic) motor or vocal tic disorder |
| 300.4 | F34.1 | Persistent depressive disorder (dysthymia) |
| V62.22 | Z91.82 | Personal history of military deployment |
| V13.59 | Z91.5 | Personal history of self-harm |
| 310.1 | F07.0 | Personality change due to another medical condition |
| V62.89 | Z60.0 | Phase of life problem |
| 292.89 | | Phencyclidine-induced anxiety disorder |
| | F16.180 | With mild use disorder |
| | F16.280 | With moderate or severe use disorder |
| | F16.980 | Without use disorder |

APPENDIX A-continued

| ICD-9-CM | ICD-10-CH | Disorder, condition, or problem |
|---|---|---|
| 292.84 | | Phencyclidine-induced bipolar and related disorder |
| | F16.14 | With mild use disorder |
| | F16.24 | With moderate or severe use disorder |
| | F16.94 | Without use disorder |
| 292.34 | | Phencyclidine-induced depressive disorder |
| | F16.14 | With mild use disorder |
| | F16.24 | With moderate or severe use disorder |
| | F16.94 | Without use disorder |
| 292.9 | | Phencyclidine-induced psychotic disorder |
| | F16.159 | With mild use disorder |
| | F16.259 | With moderate or severe use disorder |
| | F16.959 | Without use disorder |
| 292.89 | | Phencyclidine intoxication |
| | F16.129 | With mild use disorder |
| | F16.229 | With moderate or severe use disorder |
| | F16.929 | Without use disorder |
| 292.81 | | Phencyclidine intoxication delirium |
| | F16.121 | With mild use disorder |
| | F16.221 | With moderate or severe use disorder |
| | F16.921 | Without use disorder |
| | | Phencyclidine use disorder |
| 305.90 | F16.10 | Mild |
| 304.60 | F16.20 | Moderate |
| 304.60 | F16.20 | Severe |
| 307.52 | | Pica |
| | F50.8 | In adults |
| | F98.3 | In children |
| 309.81 | F43.10 | Posttraumatic stress disorder |
| 302.75 | F52.4 | Premature (early) ejaculation |
| 625.4 | N94.3 | Premenstrual dysphoric disorder |
| V62.21 | Z56.82 | Problem related to current military deployment status |
| V69.9 | Z72.9 | Problem related to lifestyle |
| V60.3 | Z60.2 | Problem related to living alone |
| V60.6 | Z59.3 | Problem related to living in a residential institution |
| V61.5 | Z64.1 | Problems related to multiparity |
| V62.5 | Z65.3 | Problems related to other legal circumstances |
| V62.5 | Z65.2 | Problems related to release from prison |
| V61.7 | Z64.0 | Problems related to unwanted pregnancy |
| 307.21 | F95.0 | Provisional tic disorder |
| 316 | F54 | Psychological factors affecting other medical conditions |
| | | Psychotic disorder due to another medical condition |
| 293.81 | F06.2 | With delusions |
| 293.82 | F06.0 | With hallucinations |
| 312.33 | F63.1 | Pyromania |
| 327.42 | G47.52 | Rapid eye movement sleep behavior disorder |
| 313.89 | F94.1 | Reactive attachment disorder |
| V61.10 | Z63.0 | Relationship distress with spouse or intimate partner |
| V62.89 | Z65.8 | Religious or spiritual problem |
| 333.94 | G25.81 | Restless legs syndrome |
| 307.53 | F98.21 | Rumination disorder |
| | | Schizoaffective disorder |
| 295.70 | F25.0 | Bipolar type |
| 295.70 | F25.1 | Depressive type |
| | F60.1 | Schizoid personality disorder |
| 295.90 | F20.9 | Schizophrenia |
| 295.40 | F20.81 | Schizophreniform disorder |
| 301.22 | F21 | Schizotypal personality disorder |
| 292.89 | | Sedative-, hypnotic-, or anxiolytic-induced anxiety disorder |
| | F13.180 | With mild use disorder |
| | F13.280 | With moderate or severe use disorder |
| | F13.980 | Without use disorder |
| 292.84 | | Sedative-, hypnotic-, or anxiolytic-induced bipolar and related disorder |
| | F13.14 | With mild use disorder |
| | F13.24 | With moderate or severe use disorder |
| | F13.94 | Without use disorder |
| | F13.921 | Sedative-, hypnotic-, or anxiolytic-induced delirium |
| 292.84 | | Sedative-, hypnotic-, or anxiolytic-induced depressive disorder |
| | F13.14 | With mild use disorder |
| | F13.24 | With moderate or severe use disorder |
| | F13.94 | Without use disorder |
| 292.82 | | Sedative-, hypnotic-, or anxiolytic-induced major neurocognitive disorder |
| | F13.27 | With moderate or severe use disorder |
| | F13.97 | Without use disorder |

APPENDIX A-continued

| ICD-9-CM | ICD-10-CH | Disorder, condition, or problem |
|---|---|---|
| 292.89 | | Sedative-, hypnotic-, or anxiolytic-induced mild neurocognitive disorder |
| | F13.288 | With moderate or severe use disorder |
| | F13.988 | Without use disorder |
| 292.9 | | Sedative-, hypnotic-, or anxiolytic-induced psychotic disorder |
| | F13.159 | With mild use disorder |
| | F13.259 | With moderate or severe use disorder |
| | F13.959 | Without use disorder |
| 292.89 | | Sedative-, hypnotic-, or anxiolytic-induced sexual dysfunction |
| | F13.181 | With mild use disorder |
| | F13.281 | With moderate or severe use disorder |
| | F13.981 | Without use disorder |
| 292.85 | | Sedative-, hypnotic-, or anxiolytic-induced sleep disorder |
| | F13.182 | With mild use disorder |
| | F13.282 | With moderate or severe use disorder |
| | F13.982 | Without use disorder |
| 292.89 | | Sedative, hypnotic, or anxiolytic intoxication |
| | F13.129 | With mild use disorder |
| | F13.229 | With moderate or severe use disorder |
| | F13.929 | Without use disorder |
| 292.81 | | Sedative, hypnotic, or anxioiytic intoxication delirium |
| | F13.121 | With mild use disorder |
| | F13.221 | With moderate or severe use disorder |
| | F13.921 | Without use disorder |
| | | Sedative, hypnotic, or anxioiytic use disorder |
| 305.40 | F13.10 | Mild |
| 304.10 | F13.20 | Moderate |
| 304.10 | F13.20 | Severe |
| 292.0 | | Sedative, hypnotic, or anxiolytic withdrawal |
| | F13.232 | With perceptual disturbances |
| | F13.239 | Without perceptual disturbances |
| 292.0 | F13.231 | Sedative, hypnotic, or anxiolytic withdrawal delirium |
| 313.23 | F94.0 | Selective mutism |
| 309.21 | F93.0 | Separation anxiety disorder |
| V65.49 | Z70.9 | Sex counseling |
| 302.83 | F65.51 | Sexual masochism disorder |
| 302.84 | F65.52 | Sexual sadism disorder |
| V61.8 | Z62.891 | Sibling relational problem |
| | | Sleep-related hypoventilation |
| 327.26 | G47.36 | Comorbid sleep-related hypoventilation |
| 327.25 | G47.35 | Congenital central alveolar hypoventilation |
| 327.24 | G47.34 | Idiopathic hypoventilation |
| 300.23 | FA0.10 | Social anxiety disorder (social phobia) |
| V62.4 | Z60.4 | Social exclusion or rejection |
| 315.39 | F80.89 | Social (pragmatic) communication disorder |
| 300.82 | F45.1 | Somatic symptom disorder |
| | | Specific learning disorder |
| 315.1 | F81.2 | With impairment in mathematics |
| 315.00 | F81.0 | With impairment in reading |
| 315.2 | F81.81 | With impairment in written expression |
| | | Specific phobia |
| 300.29 | F40.218 | Animal |
| 300.29 | | Blood-injection-injury |
| | F40.230 | Fear of blood |
| | F40.231 | Fear of injections and transfusions |
| | F40.233 | Fear of injury |
| | F40.232 | Fear of other medical care |
| 300.29 | F40.228 | Natural environment |
| 300.29 | F40.298 | Other |
| 300.29 | F40.248 | Situational |
| 315.39 | F80.0 | Speech sound disorder |
| | | Spouse or partner abuse, Psychological, Confirmed |
| 995.82 | T74.31χA | initial encounter |
| 995.82 | T74.31XD | Subsequent encounter |
| | | spouse or partner abuse, psychological, Suspected |
| 995.82 | T76.31XA | Initial encounter |
| 995.82 | T76.31XD | Subsequent encounter |
| | | Spouse or partner neglect, Confirmed |
| 995.85 | T74.01XA | initial encounter |
| 995.35 | T74.01XD | Subsequent encounter |
| | | spouse or partner neglect, suspected |
| 995.85 | T76.01XA | Initial encounter |
| 995.85 | T76.01XD | Subsequent encounter |
| | | Spouse or partner violence, Physical, Confirmed |
| 995.81 | 774.11XA | Initial encounter |

APPENDIX A-continued

| ICD-9-CM | ICD-10-CH | Disorder, condition, or problem |
|---|---|---|
| 995.81 | T74.11XD | Subsequent encounter |
| | | Spouse or partner violence, Physical, Suspected |
| 995.81 | T76.11XA | Initial encounter |
| 995.81 | T76.11XD | Subsequent encounter |
| | | Spouse or partner violence, Sexual, Confirmed |
| 995.83 | T74.21XA | Initial encounter |
| 995.83 | T74.21XD | Subsequent encounter |
| | | Spouse or partner violence, Sexual, Suspected |
| 995.83 | T76.21XA | Initial encounter |
| 995.83 | T76.21XD | Subsequent encounter |
| 307.3 | F98.4 | Stereotypic movement disorder |
| | | Stimulant intoxication (see amphetamine or cocaine intoxication for specific codes) |
| | | Stimulant use disorder (see amphetamine or cocaine use disorder for specific codes) |
| | | Stimulant withdrawal (see amphetamine or cocaine withdrawal for specific codes) |
| | | Substance intoxication delirium (see specific substances for codes) |
| | | Substance withdrawal delirium (see specific substances for codes.) |
| | | Substance/medication-induced anxiety disorder (see specific substances for codes) |
| | | Substance/medication-induced bipolar and related disorder (see specific substances for codes) |
| | | Substance/medication-induced depressive disorder (see specific substances for codes) |
| | | Substance/medication-induced major or mild neurocognitive disorder (see specific substances for codes) |
| | | Substance/medication-induced obsessive-compulsive and related disorder (see specific substances for codes) |
| | | Substance/medication-induced psychotic disorder (see specific substances for codes) |
| | | Substance/medication-induced sexual dysfunction (see specific substances for codes) |
| | | Substance/medication-induced sleep disorder (see specific substances for codes) |
| 333.99 | G25.71 | Tardive akathisia |
| 333.85 | G24.01 | Tardive dyskinesia |
| 333.72 | G24.09 | Tardive dystonia |
| V62.4 | Z60.5 | Target of (perceived) adverse discrimination or persecution |
| 292.85 | | Tobacco-induced sleep disorder |
| | F17.208 | With moderate or severe use disorder |
| | | Tobacco use disorder |
| 305.1 | Z72.0 | Mild |
| 305.1 | F17.200 | Moderate |
| 305.1 | F17.200 | Severe |
| 292.0 | F17.203 | Tobacco withdrawal |
| 307.23 | F95.2 | Tourette's disorder |
| 302.3 | F65.1 | Transvestic disorder |
| 312.39 | F63.3 | Trichotillomania (hair-pulling disorder) |
| V63.9 | Z75.3 | Unavailability or inaccessibility of health care facilities |
| V63.8 | Z75.4 | Unavailability or inaccessibility of other helping agencies |
| V62.82 | Z63.4 | Uncomplicated bereavement |
| 291.9 | F10.99 | Unspecified alcohol-related disorder |
| 300.00 | F41.9 | Unspecified anxiety disorder |
| 314.01 | F90.9 | Unspecified attention-deficit/hyperactivity disorder |
| 296.80 | F31.9 | Unspecified bipolar and related disorder |
| 292.9 | F15.99 | Unspecified caffeine-related disorder |
| 292.9 | F12.99 | Unspecified Cannabis-related disorder |
| 293.89 | F06.1 | Unspecified catatonia (code first 781.99 [R29.818] other symptoms involving nervous and musculoskeletal systems) |
| 307.9 | F80.9 | Unspecified communication disorder |
| 780.09 | R41.0 | Unspecified delirium |
| 311 | F32.9 | Unspecified depressive disorder |
| 312.9 | F91.9 | Unspecified disruptive, impulse-control, and conduct disorder |
| 300.15 | F44.9 | Unspecified dissociative disorder |
| | | Unspecified elimination disorder |
| 787.60 | R15.9 | With fecal symptoms |
| 788.30 | R32 | With urinary symptoms |
| 307.50 | F50.9 | Unspecified feeding or eating disorder |
| 302.6 | F64.9 | Unspecified gender dysphoria |
| 292.9 | F16.99 | Unspecified hallucinogen-related disorder |
| V60.9 | Z59.9 | Unspecified housing or economic problem |
| 780.54 | G47.10 | Unspecified hypersomnolence disorder |
| 292.9 | F18.99 | Unspecified inhalant-related disorder |

APPENDIX A-continued

| ICD-9-CM | ICD-10-CH | Disorder, condition, or problem |
|---|---|---|
| 780.52 | G47.00 | Unspecified insomnia disorder |
| 319 | F79 | Unspecified intellectual disability (intellectual developmental disorder) |
| 300.9 | F99 | Unspecified mental disorder |
| 294.9 | F09 | Unspecified mental disorder due to another medical condition |
| 799.59 | R41.9 | Unspecified neurocognitive disorder |
| 315.9 | F89 | Unspecified neurodevelopmental disorder |
| 300.3 | F42 | Unspecified obsessive-compulsive and related disorder |
| 292.9 | F11.99 | Unspecified opioid-related disorder |
| 292.9 | F19.99 | Unspecified other (or unknown) substance-related disorder |
| 302.9 | F65.9 | Unspecified paraphilic disorder |
| 301.9 | F60.9 | Unspecified personality disorder |
| 292.9 | F16.99 | Unspecified phencyclidine-related disorder |
| V62.9 | Z60.9 | Unspecified problem related to social environment |
| V62.9 | Z65.9 | Unspecified problem related to unspecified psychosocial circumstances |
| 298.9 | F29 | Unspecified schizophrenia spectrum and other psychotic disorder |
| 292.9 | F13.99 | Unspecified sedative-, hypnotic-, or anxiolytic-related disorder |
| 302.70 | F52.9 | Unspecified sexual dysfunction |
| 780.59 | G47.9 | Unspecified sleep-wake disorder |
| 300.82 | F45.9 | Unspecified somatic symptom and related disorder |
| 292.9 | | Unspecified stimulant-related disorder |
| | F15.99 | Unspecified amphetamine or other stimulant-related disorder |
| | F14.99 | Unspecified cocaine-related disorder |
| 307.20 | F95.9 | Unspecified tic disorder |
| 292.9 | F17.209 | Unspecified tobacco-related disorder |
| 309.9 | F43.9 | Unspecified trauma- and stressor-related disorder |
| V61.8 | Z62.29 | Upbringing away from parents |
| V62.89 | Z65.4 | Victim of crime |
| V62.89 | Z65.4 | Victim of terrorism or torture |
| 302.82 | F65.3 | Voyeuristic disorder |
| V40.31 | Z91.83 | Wandering associated with a mental disorder |

The invention claimed is:

1. A method for treating a neuropsychiatric disorder, the method comprising administering a tableted pharmaceutical composition comprising a pharmaceutically effective amount of riluzole or pharmaceutically acceptable salt thereof, gelatin as a tablet binder in an amount of 1-10% based on the total weight of the pharmaceutical composition, mannitol or sorbitol as a bulking agent in an amount of 2-4% based on the total weight of the pharmaceutical composition, and docusate sodium as a solubilizing agent in an amount of 0.01-0.5% based on the total weight of the pharmaceutical composition.

2. The method according to claim 1, wherein the pharmaceutical composition provides sublingual absorption of riluzole.

3. The method according to claim 2, wherein the pharmaceutical composition that provides sublingual absorption of riluzole is a lyophilized pharmaceutical composition.

4. The method according to claim 1, wherein the neuropsychiatric disorder is an anxiety disorder, a mood disorder, a neurodegenerative disorder, a pain disorder, ALS, a cognitive disorder, Huntington's disease, Parkinson's disease, supranuclear palsy, frontotemporal dementia, frontotemporal lobar degeneration, delirium, Alzheimer's disease, mild cognitive impairment, mild cognitive impairment due to Alzheimer's disease, ataxia, hereditary ataxia, depression, mania, attention deficit disorder, drug addiction, dementia, agitation, apathy, anxiety, psychoses, post-traumatic stress disorder, irritability, and disinhibition, learning disorder, memory loss, mental retardation, Rett Syndrome, tinnitus, a personality disorder, a bipolar disorder, an obsessive-compulsive disorder, an eating disorder, a conduct disorder in DSM-5, and or a combination thereof.

5. The method according to claim 4, wherein the neuropsychiatric symptom is anxiety, depression, stress, fatigue, feeling of panic, fear, uneasiness, problem in sleeping, cold or sweaty hands and/or feet, mood liability, mania, impaired concentration or attention, a cognitive problem, obsession, compulsion, repetitive behavior, aggression, social phobias or impairment, stage fight, shortness of breath, heart palpitations, an inability to be still and calm, dry mouth, numbness or tinging in the hands or feet, nausea, muscle tension, dizziness apathy, elation, disinhibition, irritability, wandering, irritable bowel, belly pain, belly discomfort, diarrhea, change in bowel habits, abdominal bloating, abdominal gas, abdominal bloating, constipation or a combination thereof.

6. The method according to claim 1, wherein the pharmaceutical composition further comprises a sweetener.

7. The method according to claim 6, wherein the sweetener comprises sucralose.

8. The method according to claim 1, wherein the pharmaceutical composition further comprises a flavoring agent.

9. The method according to claim 1, wherein the formulation provides an AUC at a dose of 35 mg of from 110% to 180% of the AUC of an oral tablet formulation at a dose of 50 mg, said AUC being measured at 0.5 hours, 1 hour or 2 hours after administration.

10. The method according to claim 1, wherein the formulation produces a rapid therapeutic onset of action within about 10 minutes after administration.

11. The method according to claim 1, wherein the formulation is associated with minimal or no oral numbness, or said oral numbness dissipates in less than 30 minutes.

12. The method according to claim 1, wherein the liver function abnormalities side effects of riluzole are attenuated relative to those which are associated with the orally administered riluzole.

13. The method according to claim 1, wherein the formulation is dosed at or below about 50 mg/day.

14. The method according to claim 1, wherein the formulation is dosed at or below about 35 mg/day.

* * * * *